(12) United States Patent
Wu

(10) Patent No.: US 6,498,146 B1
(45) Date of Patent: *Dec. 24, 2002

(54) ERYTHROMYCIN DERIVATIVES

(75) Inventor: Yong-Jin Wu, Madison, CT (US)

(73) Assignee: Pfizer Inc, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/688,679

(22) Filed: Oct. 16, 2000

Related U.S. Application Data

(60) Provisional application No. 60/162,289, filed on Oct. 28, 1999.

(51) Int. Cl.$^7$ .................. A61K 31/70; C07H 17/08
(52) U.S. Cl. ................................ 514/29; 536/7.4
(58) Field of Search .................. 536/7.4; 512/29

(56) References Cited

U.S. PATENT DOCUMENTS

| 6,159,945 A | * | 12/2000 | Wu | 514/29 |
| 6,169,168 B1 | * | 1/2001 | Asaka et al. | 536/7.4 |
| 6,291,656 B1 | * | 9/2001 | Wu | 536/7.4 |

* cited by examiner

Primary Examiner—Elli Peselev
(74) Attorney, Agent, or Firm—Peter C. Richardson; Paul H. Ginsburg; Israel Nissenbaum

(57) ABSTRACT

The invention relates to compounds of the formula 1, 2, and 3 and to pharmaceutically acceptable salts and prodrugs thereof, wherein the groups are as defined herein. The invention also relates to pharmaceutical compositions containing the compounds of formula I, methods of using said compounds of formula 1, 2, and 3 the treatment of infections, and methods of preparing said compounds of formula 1, 2, and 3.

36 Claims, No Drawings

ERYTHROMYCIN DERIVATIVES

This application is a non-provisional filing of provisional application Ser. No. 60/162,289, filed Oct. 28, 1999.

BACKGROUND OF THE INVENTION

This invention relates to novel tricyclic erythromycin derivatives. The compounds of this invention are useful as antibiotic agents in mammals, including man, as well as in fish and birds. The compounds of the present invention are broad-spectrum macrolide antibiotics that are effective against infections caused by certain gram-positive and gram-negative bacteria as well as protozoa. Various derivatives of erythromycin A, useful as antibiotic agents, are referred to in U.S. patent application Ser. No. 60/049,349, filed Jun. 11, 1997, and U.S. application Ser. No. 09/355092, filed Jul. 20, 1999, both of which are incorporated herein by reference in their entirety, and in U.S. patent application Ser. No. 60/063,676, entitled "9-Amino-3-Keto Erythromycin Derivatives", (Yong-Jin Wu), filed Oct. 29, 1997, which is incorporated herein by reference thereto, in its entirety.

SUMMARY OF THE INVENTION

The present invention relates to compounds of the formula I

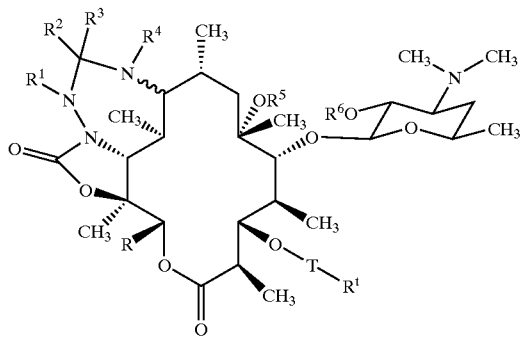

1 and to pharmaceutically acceptable salts and prodrugs thereof, wherein:

R is $C_1$–$C_{10}$ alkyl, $C_3$–$C_{10}$ alkenyl, $C_3$–$C_{10}$ alkynyl, or $C_3$–$C_{10}$ cycloalkyl, wherein up to two carbons of said alkyl, cycloalkyl, alkenyl, alkynyl are optionally replaced by one or more heteroatoms selected from O, S and N, and are optionally substituted by one or more substituents (preferably one to four substituents), said substituents being selected from the group (hereinafter also referred to as "Group A") consisting of:
 (a) nitro;
 (b) $N_3$;
 (c) CN;
 (d) $C_1$–$C_{10}$ alkoxy;
 (e) $C_1$–$C_{10}$ alkanoyl;
 (f) $C_1$–$C_{10}$ alkyl;
 (g) $C_2$–$C_{10}$ alkenyl;
 (h) $C_2$–$C_{10}$ alkynyl;
 (i) $C_3$–$C_{10}$ cycloalkyl;
 (j) 4 to 10 membered heterocyclic;
 (k) —$C(O)R^{10}$;
 (l) —$C(O)OR^{10}$;
 (m) —$NR^{10}R^{11}$;
 (n) —$NHC(O)R^{10}$;
 (o) —$NHC(O)NR^{10}R^{11}$;
 (p) —$S(O)_n$, wherein n is 0,1, or 2;
 (q) —$SO_2R^{10}$; and
 (r) —$SO_2NR^{10}R^{11}$;

each $R^1$, $R^2$, $R^3$, and $R^4$ is independently selected from H, $C_1$–$C_{12}$ $C_3$–$C_{10}$ alkenyl, $C_3$–$C_{10}$ alkynyl, and —$(CR^8R^9)_mZ$, with m being an integer from 0 to 6; wherein up to two carbons of said alkyl, alkenyl, alkynyl are optionally replaced by a heteroatom selected from O, S and N, and are optionally substituted by one or more substituents (preferably from one to four substituents), selected from Group A;

or $R^2$ and $R^3$, together with the carbon to which they are attached, form a 3–10 membered ring; the ring carbons are optionally substituted by one or more heteroatoms selected from O, S and N;

$R^5$ is selected from $C_1$–$C_{10}$ alkyl, $C_3$–$C_{10}$ alkenyl, $C_3$–$C_{10}$ alkynyl, —$CH_2$—$CH$=$CH$—Z, and —$(CR^9R^{10})_mZ$; with m being an integer from 1 to 6; wherein the alkyl, alkenyl and alkynyl can be substituted with one or more substituents (preferably from one to four substituents) selected from Group A;

$R^6$ is H, —$C(O)O(C_1$–$C_{18})$ alkyl or —$C(O)(C_1$–$C_{18})$ alkyl, wherein one or more carbons of either of said alkyl may be replaced by a heteroatom selected from O, S and N;

each $R^8$ and $R^9$ is independently selected from H, halo, and $C_1$–$C_6$ alkyl; or $R^8$ and $R^9$, together with the carbon to which they are attached, can form a 3 to 10 membered cyclic or heterocyclic di-radical;

each $R^{10}$ and $R^{11}$ is independently H, $C_1$–$C_{12}$ alkyl, aryl substituted $C_1$–$C_{12}$ alkyl, or heteroaryl substituted $C_1$–$C_{12}$ alkyl, wherein one or more carbons of said alkyl are optionally replaced by a heteroatom selected from O, S and N.

each Z is independently 4–10 membered heterocyclic or $C_6$–$C_{10}$ aryl, wherein said heterocyclic and aryl groups are optionally substituted by one or more substituents (preferably one to four substituents) selected from Group A;

T is absent or selected from the group consisting of:
 (a) —$C(O)$—,
 (b) —$C(O)$—$O$—,
 (c) —$CH_2$—,
 (d) —$C(S)$—$S$—,
 (e) —$C(O)$—$NR^{10}$—;
 (f) —$S(O)_n$—, where n is 0,1, or 2,
 (g) —$S(O)_n$—$O$—, wherein n is 0, 1, or 2,
 (h) —$P(O)(OR^{10})_n$—, wherein n is 0, 1, or 2, and
 (i) —$S(O)_2$—$NR^{10}$—, $R^t$ is selected from the group consisting of: $C_1$–$C_6$ alkyl, $C_3$–$C_6$ alkenyl, $C_3$–$C_{12}$ cycloalkyl, aryl, heteroaryl, and heterocycloalkyl, wherein said alkyl, alkenyl, cycloalkyl, aryl, heteroaryl, and heterocycloalkyl groups are optionally substituted by one or more substituents (preferably one to four substituents) selected from Group A.

The present invention also relates to compounds of formula 2:

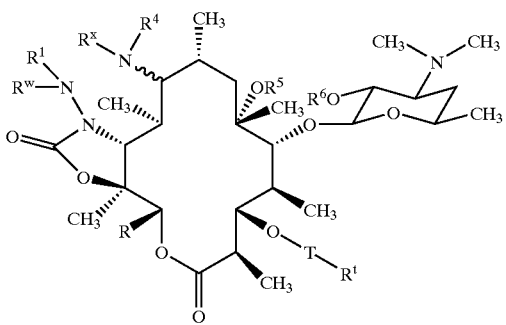

and to pharmaceutically acceptable salts and prodrugs thereof, wherein:

each $R^w$ and $R^x$ is independently H, $C_1$–$C_{10}$ alkyl, $C_3$–$C_{10}$ alkenyl, $C_3$–$C_{10}$ alkynyl, or $C_3$–$C_{10}$ cycloalkyl, wherein up to two carbons of said alkyl, cycloalkyl, alkenyl, alkynyl are optionally replaced by one or more heteroatoms selected from O, S and N, and are optionally substituted by one or more substituents (preferably one to four substituents) selected from Group A;

$R^1$ is as defined for formula 1, or $R^1$ and $R^w$ together with the nitrogen to which they are attached can form —N=C($R^1$)($R^2$), or form a 3–10 membered ring; the ring carbons are optionally substituted by one or more heteroatoms selected from O, S and N, $R^4$ is as defined for formula 1, or $R^4$ and $R^x$, together with the nitrogen to which they are attached, form —N=C($R^4$)($R^2$), or form a 3–10 membered ring; the ring carbons are optionally substituted by one or more heteroatoms selected from O, S and N, R, $R^5$, $R^6$, $R^t$ and T are as defined for formula 1.

The present invention also relates to compounds of formula 3:

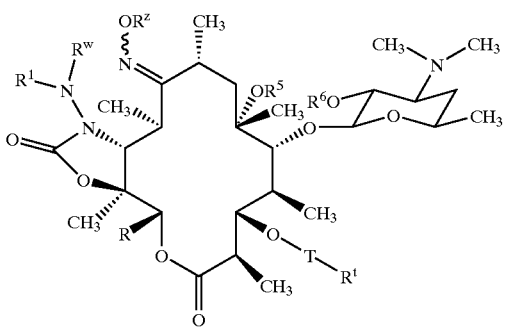

and to pharmaceutically acceptable salts and prodrugs thereof, wherein:

$R^w$ is H, $C_1$–$C_{10}$ alkyl, $C_3$–$C_{10}$ alkenyl, $C_3$–$C_{10}$ alkynyl, $C_3$–$C_{10}$ cycloalkyl, wherein one or two carbons of said alkyl, cycloalkyl, alkenyl, alkynyl are optionally replaced by one or more heteroatoms selected from O, S and N, and are optionally substituted by one or more substituents (preferably 1–4 substitutents) selected from Group A;

$R^z$ is H, $C_1$–$C_{10}$ alkyl, $C_3$–$C_{10}$ alkenyl, $C_3$–$C_{10}$ alkynyl, $C_3$–$C_{10}$ cycloalkyl, wherein one or two carbons of said alkyl, cycloalkyl, alkenyl, alkynyl are optionally replaced by one or more heteroatoms selected from O, S and N, and are optionally substituted by one or more substituents (preferably one to four substituents) selected from Group A;

R, $R^1$, $R^5$, $R^6$, $R^t$ and T are as defined for formula 1.

A first embodiment of the invention is a compound having the formula 1, as described above, and a preferred embodiment is a compound of formula 1 wherein R=Et, $R^2$=$R^3$=$R^4$=$R^6$=H, $R^5$=Me, and $R^1$=—(CH$_2$)$_3$Z.

Representative compounds of the invention having formula 1 are those selected from the group consisting of:

Compounds of formula 1, wherein R=Et, $R^1$=$R^2$=$R^3$=$R^4$=$R^6$=H, $R^5$=—(CH$_2$)—CH=CH—Z, Z is quinolin-2-yl, quinolin-3-yl, quinolin-4-yl, quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is absent, $R^t$ is H, acetyl, (4-methoxy)benzoyl, or methanesulfonyl, Compounds of formula 1, wherein R=Et, $R^1$=$R^2$=$R^3$=$R^4$=$R^6$=H, $R^5$=—(CH$_2$)—CH=CH—Z, Z is quinolin-2-yl, quinolin-3-yl, quinolin-4-yl , quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is —S(O)$_2$, $R^t$ is —CH=CH$_2$, —CH$_2$CH$_2$N(CH$_3$)$_2$, or —CH$_2$CH$_2$S-phenyl, Compounds of formula 1, wherein R=Et, $R^1$=$R^2$=$R^3$=$R^4$=$R^6$=H, $R^5$=—(CH$_2$)—CH=CH—Z, Z is quinolin-2-yl, quinolin-3-yl, quinolin-4-yl , quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is —C(O)—NH, $R^t$ is (2-nitrophenyl), phenyl, allyl, —CH(CH$_3$)$_2$, or cyclohexyl, Compounds of formula 1, wherein R=Et, $R^1$=Me, $R^2$=$R^3$=$R^4$=$R^6$=H, $R^5$=—(CH$_2$)—CH=CH—Z, Z is quinolin-2-yl, quinolin-3-yl, quinolin-4-y, quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is absent, $R^t$ is H, acetyl, (4-methoxy)benzoyl, or methanesulfonyl, Compounds of formula 1, wherein R=Et, $R^1$=Me, $R^2$=$R^3$=$R^4$=$R^6$=H, $R^5$=—(CH$_2$)—CH=CH—Z, Z is quinolin-2-yl, quinolin-3-yl, quinolin-4-yl, quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is —S(O)$_2$, $R^t$ is —CH=CH$_2$, —CH$_2$CH$_2$N(CH$_3$)$_2$, or —CH$_2$CH$_2$S-phenyl, Compounds of formula 1, wherein R=Et, $R^1$=Me, $R^2$=$R^3$=$R^4$=$R^6$=H, $R^5$=—(CH$_2$)—CH=CH—Z, Z is quinolin-2-yl, quinolin-3-yl, quinolin-4-yl, quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is —C(O)—NH, $R^t$ is (2-nitrophenyl), phenyl, allyl, —CH(CH$_3$)$_2$, or cyclohexyl, Compounds of formula 1, wherein R=Et, $R^4$=Me, $R^1$=$R^2$=$R^3$=$R^6$=H, $R^5$=—(CH$_2$)—CH=CH—Z, Z is quinolin-2-yl, quinolin-3-yl, quinolin-4-yl, quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is absent, $R^t$ is H, acetyl, (4-methoxy)benzoyl, or methanesulfonyl, Compounds of formula 1, wherein R=Et, $R^4$=Me, $R^1$=$R^2$=$R^3$=$R^6$=H, $R^5$=—(CH$_2$)—CH=CH—Z, Z is quinolin-2-yl, quinolin-3-yl, quinolin-4-yl, quinolin-5-yl, quinolin-6-yl, quinolin-7-yl, quinolin-8-yl, 4-phenyl-1- imidazol-1-yl, imidazo(4,5-b)pyridin-3-yl, or 4-pyridin-3-yl-imidazol-1-yl, T is —S(O)$_2$—, $R^t$ is —CH═CH$_2$, —CH$_2$CH$_2$N(CH$_3$)$_2$, or —CH$_2$CH$_2$S-phenyl, Compounds of formula 1, wherein R=Et, $R^4$=Me, $R^1$=$R^2$=$R^3$=$R^6$=H, $R^5$=—(CH$_2$)—CH═CH—Z, Z is quinolin-2-yl, quinolin-3-yl, quinolin-4-yl, quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is —C(O)—NH, $R^t$ is (2-nitrophenyl), phenyl, allyl, —CH(CH$_3$)$_2$, or cyclohexyl, Compounds of formula 1, wherein R=Et, $R^2$=$R^3$=Me, $R^1$=$R^4$=$R^6$=H, $R^5$=—(CH$_2$)—CH═CH—Z, Z is quinolin-2-yl, quinolin-3-yl, quinolin-4-yl, quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is absent, $R^t$ is H, acetyl, (4-methoxy)benzoyl, or methanesulfonyl, Compounds of formula 1, wherein R=Et, $R^2$=$R^3$=Me, $R^1$=$R^4$=$R^6$=H, $R^5$=—(CH$_2$)—CH═CH—Z, Z is quinolin-2-yl, quinolin-3-yl, quinolin-4-yl, quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is —S(O)$_2$, $R^t$ is —CH═CH$_2$, —CH$_2$CH$_2$N(CH$_3$)$_2$, or —CH$_2$CH$_2$S-phenyl, Compounds of formula 1, wherein R=Et, $R^2$=$R^3$=Me, $R^1$=$R^4$=$R^6$=H, $R^5$=—(CH$_2$)—CH═CH—Z, Z is quinolin-2-yl, quinolin-3-yl, quinolin-4-yl, quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, TT is —C(O)—NH, $R^t$ is (2-nitrophenyl), phenyl, allyl, —CH(CH$_3$)$_2$, or cyclohexyl, Compounds of formula 1, wherein R=Et, $R^1$=$R^2$=$R^3$=$R^4$=$R^6$=H, $R^5$=Me, $R^1$=—(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is absent, $R^t$ is acetyl, Compounds of formula 1, wherein R=Et, $R^2$=$R^3$=$R^4$=$R^6$=H, $R^5$=Me, $R^1$=—(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is absent, $R^t$ is acetyl, Compounds of formula 1, wherein R=Et, $R^2$=$R^3$=$R^4$=$R^6$=H, $R^5$=Me, $R^1$=—(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is absent, $R^t$ is (4-methoxy)benzoyl, Compounds of formula 1, wherein R=Et, $R^2$=$R^3$=$R^4$=$R^6$=H, $R^5$=Me, $R^1$=—(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is absent, $R^t$ is methanesulfonyl, Compounds of formula 1, wherein R=Et, $R^2$=$R^3$=$R^4$=$R^6$=H, $R^5$=Me, $R^1$=—(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is —S(O)$_2$—, $R^t$ is —CH═CH$_2$, Compounds of formula 1, wherein R=Et, $R^2$=$R^3$=$R^4$=$R^6$=H, $R^5$=Me, $R^1$=—(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is —S(O)$_2$—, $R^t$ is —CH$_2$CH$_2$N(CH$_3$)$_2$, Compounds of formula 1, wherein R=Et, $R^2$=$R^3$=$R^4$=$R^6$=H, $R^5$=Me, $R^1$=—(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is —S(O)$_2$—, $R^t$ is —CH$_2$CH$_2$—S-phenyl, Compounds of formula 1, wherein R=Et, $R^2$=$R^3$=$R^4$=$R^6$=H, $R^5$=Me, $R^1$=—(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is —C(O)—NH—, $R^t$ is (2-nitrophenyl), Compounds of formula 1, wherein R=Et, $R^2$=$R^3$=$R^4$=$R^6$=H, $R^5$=Me, $R^1$=—(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is —C(O)—NH—, $R^t$ is phenyl, Compounds of formula 1, wherein R=Et, $R^2$=$R^3$=$R^4$=$R^6$=H, $R^5$=Me, $R^1$=—(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is —C(O)NH—, $R^t$ is allyl, Compounds of formula 1, wherein R=Et, $R^2$=$R^3$=$R^4$=$R^6$=H, $R^5$=Me, $R^1$=—(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is —C(O)—NH—, $R^t$ is CH(CH$_3$)$_2$, Compounds of formula 1, wherein R=Et, $R^2$=$R^3$=$R^4$=$R^6$=H, $R^5$=Me, $R^1$=—(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is —C(O)—NH—, $R^t$ is cyclohexyl, the pharmaceutically acceptable salts and prodrugs of the foregoing compounds.

A second embodiment of the invention is a compound having the formula 2 as described above and a preferred embodiment is a compound of formula 2 wherein R=Et, $R^w$=$R^x$=$R^4$=$R^6$=H, $R^5$=Me, $R^1$=—(CH$_2$)$_3$Z.

Representative compounds of the invention having formula 2 are those selected from the group consisting of:

Compounds of formula 2, wherein R=Et, $R^1$=$R^w$=$R^x$=$R^4$=$R^6$=H, $R^5$=—(CH$_2$)—CH═CH—Z, Z is quinolin-2-yl, quinolin-3-yl, quinolin-4-yl, quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is absent, $R^t$ is H, acetyl, (4-methoxy)benzoyl, or methanesulfonyl Compounds of formula 2, wherein R=Et, $R^1$=$R^w$=$R^x$=$R^4$=$R^6$=H, $R^5$=—(CH$_2$)—CH═CH—Z, Z is quinolin-2-yl, quinolin-3-yl, quinolin-4-yl, quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is —S(O)$_2$, $R^t$ is —CH═CH$_2$, —CH$_2$CH$_2$N(CH$_3$)$_2$, or —CH$_2$CH$_2$S-phenyl, Compounds of formula 2, wherein R=Et, $R^1$=$R^w$=$R^x$=$R^4$=$R^6$=H, $R^5$=—(CH$_2$)—CH═CH—Z, Z is quinolin-2-yl, quinolin-3-yl, quinolin-4-yl, quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is —C(O)—NH, $R^t$ is (2-nitrophenyl), phenyl, allyl, —CH(CH$_3$)$_2$, or cyclohexyl, Compounds of formula 2, wherein R=Et, $R^w$=$R^x$=$R^4$=$R^6$=H, $R^5$=Me, $R^1$=—(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is absent, $R^t$ is acetyl, Compounds of formula 2, wherein R=Et, $R^w$=$R^x$=$R^4$=$R^6$=H, $R^5$=Me, $R^1$=—(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is absent, $R^t$ is acetyl, Compounds of formula 2, wherein R=Et, $R^w=R^x=R^4=R^6=$H, $R^5$=Me, $R^1$=—$(CH_2)_3$Z, Z is quinolin-4-yl, 4-phenyl-1-imidazol-1-yl, imidazo(4,5-b)pyridin-3-yl, or 4-pyridin-3-yl-imidazol-1-yl, T is absent, $R^t$ is (4-methoxy)benzoyl, Compounds of formula 2, wherein $R^w=R^x=R^4=R^6$=H, $R^5$=Me, $R^1$=—$(CH_2)_3$Z, Z is quinolin-4-yl, 4-phenyl-1-imidazol-1-yl, imidazo(4,5-b)pyridin-3-yl, or 4-pyridin-3-yl-imidazol-1-yl, T is absent, $R^t$ is methanesulfonyl, Compounds of formula 2, wherein $R^w=R^x=R^4=R^6$=H, $R^5$=Me, $R^1$=—$(CH_2)_3$Z, Z is quinolin-4-yl, 4-phenyl-1-imidazol-1-yl, imidazo(4,5-b)pyridin-3-yl, or 4-pyridin-3-yl-imidazol-1-yl, T is —$S(O)_2$—, $R^t$ is —CH=$CH_2$, Compounds of formula 2, wherein R=Et, $R^w=R^x=R^4=R^6=$ H, $R^5$=Me, $R^1$=—$(CH_2)_3$Z, Z is quinolin-4-yl, 4-phenyl-1-imidazol-1-yl, imidazo(4,5-b)pyridin-3-yl, or 4-pyridin-3-yl-imidazol-1-yl, T is —$S(O)_2$—, $R^t$ is —$CH_2CH_2N(CH_3)_2$, Compounds of formula 2, wherein R=Et, $R^w=R^x=R^4=R^6=$ H, $R^5$=Me, $R^1$=—$(CH_2)_3$Z, Z is quinolin-4-yl, 4-phenyl-1-imidazol-1-yl, imidazo(4,5-b)pyridin-3-yl, or 4-pyridin-3-yl-imidazol-1-yl, T is —$S(O)_2$—, $R^t$ is —$CH_2CH_2$—S-phenyl, Compounds of formula 2, wherein R=Et, $R^w=R^x=R^4=R^6=$ H, $R^5$=Me, $R^1$=—$(CH_2)_3$Z, Z is quinolin-4-yl, 4-phenyl-1-imidazol-1-yl, imidazo(4,5-b)pyridin-3-yl, or 4-pyridin-3-yl-imidazol-1-yl, T is —C(O)—NH—, $R^t$ is (2-nitrophenyl), Compounds of formula 2, wherein R=Et, $R^w=R^x=R^4=R^6=$ H, $R^5$=Me, $R^1$=—$(CH_2)_3$Z, Z is quinolin-4-yl, 4-phenyl-1-imidazol-1-yl, imidazo(4,5-b)pyridin-3-yl, or 4-pyridin-3-yl-imidazol-1-yl, T is —C(O)—NH—, $R^t$ is phenyl, Compounds of formula 2, wherein R=Et, $R^w=R^x=R^4=R^6=$ H, $R^5$=Me, $R^1$=—$(CH_2)_3$Z, Z is quinolin-4-yl, 4-phenyl-1-imidazol-1-yl, imidazo(4,5-b)pyridin-3-yl, or 4-pyridin-3-yl-imidazol-1-yl, T is —C(O)NH—, $R^t$ is allyl, Compounds of formula 2, wherein R=Et, $R^w=R^x=R^4=R^6=$ H, $R^5$=Me, $R^1$=—$(CH_2)_3$Z, Z is quinolin-4-yl, 4-phenyl-1-imidazol-1-yl, imidazo(4,5-b)pyridin-3-yl, or 4-pyridin-3-yl-imidazol-1-yl, T is —C(O)—NH—, $R^t$ is $CH(CH_3)_2$, Compounds of formula 2, wherein R=Et, $R^w=R^x=R^4=R^6=$ H, $R^5$=Me, $R^1$=—$(CH_2)_3$Z, Z is quinolin-4-yl, 4-phenyl-1-imidazol-1-yl, imidazo(4,5-b)pyridin-3-yl, or 4-pyridin-3-yl-imidazol-1-yl, T is —C(O)—NH, $R^t$ is cyclohexyl, the pharmaceutically acceptable salts and prodrugs of the foregoing compounds.

A third embodiment of the invention is a compound having the formula 3 as described above and a preferred embodiment is a compound of formula 3 wherein R=Et, $R^w=R^6$=H, $R^5=R^z$=Me, $R^1$=—$(CH_2)_3$Z.

Representative compounds of the invention having formula 3 are those selected from the group consisting of:

Compounds of formula 3, wherein R=Et, $R^1=R^w=R^6$=H, $R^z$=Me, $R^5$=—$(CH_2)$—CH=CH—Z, Z is quinolin-2-yl, quinolin-3-yl, quinolin-4-yl, quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is absent, $R^t$ is H, acetyl, (4-methoxy)benzoyl, or methanesulfonyl, Compounds of formula 3, wherein R=Et, $R^1=R^w=R^6$=H, $R^z$=Me, $R^5$=—$(CH_2)$—CH=CH—Z, Z is quinolin-2-yl, quinolin-3-yl, quinolin-4-yl , quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is —$S(O)_2$, $R^t$ is —CH=$CH_2$, —$CH_2CH_2N(CH_3)_2$, or —$CH_2CH_2$S-phenyl, Compounds of formula 3, wherein R=Et, $R^1=R^w=R^6$=H, $R^z$=Me, $R^5$=—$(CH_2)$—CH=CH—Z, Z is quinolin-2-yl, quinolin-3-yl, quinolin-4-yl, quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is —C(O)—NH, $R^t$ is (2-nitrophenyl), phenyl, allyl, $CH(CH_3)_2$, or cyclohexyl, Compounds of formula 3, wherein R=Et, $R^w=R^6$=H, $R^5=R^z$=Me, $R^1$=—$(CH_2)_3$Z, Z is quinolin-4-yl, 4-phenyl-1-imidazol-1-yl, imidazo(4,5-b)pyridin-3yl, or 4-pyridin-3-yl-imidazol-1-yl, T is absent, $R^t$ is acetyl, Compounds of formula 3, wherein R=Et, $R^w=R^6$=H, $R^5=R^z$=Me, $R^1$=—$(CH_2)_3$Z, Z is quinolin-4-yl, 4-phenyl-1-imidazol-1-yl, imidazo(4,5-b)pyridin-3-yl, or 4-pyridin-3-yl-imidazol-1-yl, T is absent, $R^t$ is (4-methoxy)benzoyl, Compounds of formula 3, wherein R=Et, $R^w=R^6$=H, $R^5=R^z$=Me, $R^1$=—$(CH_2)_3$Z, Z is quinolin-4-yl, 4-phenyl-1-imidazol-1-yl, imidazo(4,5-b)pyridin-3-yl, or 4-pyridin-3-yl-imidazol-1-yl, T is absent, $R^t$ is methanesulfonyl, Compounds of formula 3, wherein R=Et, $R^w=R^6$=H, $R^5=R^z$=Me, $R^1$=$(CH_2)_3$Z, Z is quinolin-4-yl, 4-phenyl-1-imidazol-1-yl, imidazo(4,5-b)pyridin-3-yl, or 4-pyridin-3-yl-imidazol-1-yl, T is —$S(O)_2$—, $R^t$ is —CH=$CH_2$, Compounds of formula 3, wherein R=Et, $R^w=R^6$=H, $R^5=R^z$=Me, $R^1$=—$(CH_2)_3$Z, Z is quinolin-4-yl, 4-phenyl-1-imidazol-1-yl, imidazo(4,5-b)pyridin-3-yl, or 4-pyridin-3-yl-imidazol-1-yl, T is —$S(O)_2$—, $R^1$ is —$CH_2CH_2N(CH_3)_2$, Compounds of formula 3, wherein R=Et, $R^w=R^6$=H, $R^5=R^z$=Me, $R^1$=$(CH_2)_3$Z, Z is quinolin-4-yl, 4-phenyl-1-imidazol-1-yl, imidazo(4,5-b)pyridin-3-yl, or 4-pyridin-3-yl-imidazol-1-yl, T is —$S(O)_2$—, $R^t$ is $CH_2CH_2$—S-phenyl, Compounds of formula 3, wherein R=Et, $R^w=R^6$=H, $R^5=R^z$=Me, $R^1$=—$(CH_2)_3$Z, Z is quinolin-4-yl, 4-phenyl-1-imidazol-1-yl, imidazo(4,5-b)pyridin-3-yl, or 4-pyridin-3-yl-imidazol-1-yl, T is —C(O)—NH—, $R^t$ is (2-nitrophenyl), Compounds of formula 3, wherein R=Et, $R^w=R^6$=H, $R^5=R^z$=Me, $R^1$=—$(CH_2)_3$Z, Z is quinolin-4-yl, 4-phenyl-1-imidazol-1-yl, imidazo(4,5-b)pyridin-3-yl, or 4-pyridin-3-yl-imidazol-1-yl, T is —C(O)—NH—, $R^t$ is phenyl, Compounds of formula 3, wherein R=Et, $R^w=R^6$=H, $R^5=R^z$=Me, $R^1$=—$(CH_2)_3$Z, Z is quinolin-4-yl, 4-phenyl-1-imidazol-1-yl, imidazo(4,5-b)pyridin-3-yl, or 4-pyridin-3-yl-imidazol-1-yl, T is —C(O)—NH—, $R^t$ is allyl, Compounds of formula 3, wherein R=Et, $R^w=R^6$=H, $R^5=R^z$=Me, $R^1$=—$(CH_2)_3$Z, Z is quinolin-4-yl, 4-phenyl-1-imidazol-1-yl, imidazo(4,5-b)pyridin-3-yl, or 4-pyridin-3-yl-imidazol-1-yl, T is —C(O)—NH—, R' is —CH(CH$_3$)$_2$, Compounds of formula 3, wherein R=Et, R$^w$=R$^6$=H, R$^5$=R$^z$=Me, R$^1$=—(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is —C(O)—NH—, R' is cyclohexyl, the pharmaceutically acceptable salts and prodrugs of the foregoing compounds.

The invention also relates to a pharmaceutical composition for the treatment of a bacterial infection or protozoa infection in a mammal, fish, or bird which comprises a therapeutically effective amount of a compound of formulas 1–3, or a pharmaceutically acceptable salt thereof, or a prodrug thereof, and a pharmaceutically acceptable carrier.

The invention also relates to a method of treating a bacterial infection or a protozoa infection in a mammal, fish, or bird which comprises administering to said mammal, fish or bird a therapeutically effective amount of a compound of formulas 1–3 or a pharmaceutically acceptable salt or prodrug thereof.

The term "treatment", as used herein, unless otherwise indicated, includes the treatment or prevention of a bacterial infection or protozoa infection as provided in the method of the present invention.

The invention also relates to a method of preparing compounds of formulas 1–3

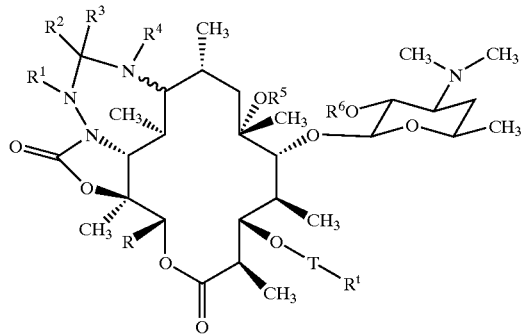

1 and pharmaceutically acceptable salts thereof, wherein R, R$^1$–R$^6$, R' and T are as defined above. The compound of formula 1 is prepared as follows: treating a compound of the formula 7

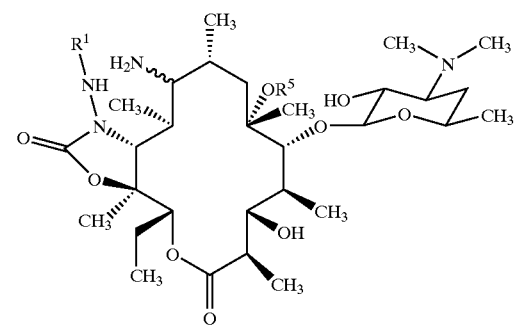

7 with a compound of formula R$^2$R$^3$C(=O) in the presence of an acid in a solvent. The preferred acids are formic acid, acetic acid, p-toluenesulfonic acid and the preferred solvents are THF, dichloromethane, and chloroform.

Patients that can be treated with the compounds of formulas 1–3, and/or the pharmaceutically acceptable salts and prodrugs thereof, include mammals (particularly humans), fish, and birds suffering from infections caused by various micro-organisms including Gram positive and Gram negative bacteria.

As used herein, unless otherwise indicated, the term "bacterial infection(s)" or "protozoa infections" includes bacterial infections and protozoa infections which occur in mammals, fish and birds as well as disorders related to bacterial infections and protozoa infections that may be treated or prevented by administering antibiotics such as the compounds of the present invention. Such bacterial infections and protozoa infections and disorders related to such infections include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus,* or Peptostreptococcus spp.; pharynigitis, rheumatic fever, and glomerulonephritis related to infection by *Streptococcus pyogenes,* Groups C and G streptococci, *Clostridium diptheriae,* or *Actinobacillus haemolyticum;* respiratory tract infections related to infection by *Mycoplasma pneumoniae, Legionella pneumophila, Streptococcus pneumoniae, Haemophilus influenzae,* or *Chlamydia pneumoniae;* uncomplicated skin and soft tissue infections, abscesses and osteomyelitis, and puerperal fever related to infection by *Staphylococcus aureus,* coagulase-positive staphylococci (i.e., *S. epidermidis, S. hemolyticus,* etc.), *Streptococcus pyogenes, Streptococcus agalactiae,* Streptococcal groups C-F (minute-colony streptococci), viridans streptococci, *Corynebacterium minutissimum,* Clostridium spp., or *Bartonella henselae;* uncomplicated acute urinary tract infections related to infection by *Staphylococcus saprophyticus* or Enterococcus spp.; urethritis and cervicitis; and sexually transmitted diseases related to infection by *Chlamydia trachomatis, Haemophilus ducreyi, Treponema pallidum, Ureaplasma urealyticum,* or *Neiserria gonorrheae;* toxin diseases related to infection by *S. aureus* (food poisoning and Toxic shock syndrome), or Groups A, B, and C streptococci; ulcers related to infection by *Helicobacter pylori;* systemic febrile syndromes related to infection by *Borrelia recurrentis;* Lyme disease related to infection by *Borrelia burgdorferi;* conjunctivitis, keratitis, and dacrocystitis related to infection by *Chlamydia trachomatis, Neisseria gonorrhoeae, S. aureus, S. pneumoniae, S. pyogenes, H. influenzae,* or Listeria spp.; disseminated *Mycobacterium avium* complex (MAC) disease related to infection by *Mycobacterium avium,* or *Mycobacterium intracellulare;* gastroenteritis related to infection by *Campylobacter jejuni;* intestinal protozoa related to infection by Cryptosporidium spp.; odontogenic infection related to infection by viridans streptococci; persistent cough related to infection by *Bordetella pertussis;* gas gangrene related to infection by *Clostridium perfringens* or Bacteroides spp.; and atherosclerosis related to infection by *Helicobacter pylori* or *Chlamydia pneumoniae.* Bacterial infections and protozoa infections and disorders related to such infections that may be treated or prevented in animals include the following: bovine respiratory diseases related to infection by *P. haem., P. multocida, Mycoplasma bovis,* or Bordetella spp.; cow enteric disease related to infection by *E. coli* or protozoa (i.e., *coccidia, cryptosporidia,* etc.); dairy cow mastitis related to infection by *Staph. aureus, Strep. uberis, Strep. agalactiae, Strep. dysgalactiae,* Klebsiella spp., Corynebacterium, or Enterococcus spp.; swine respiratory disease related to infection by *A. pleuro., P. multocida,* or Mycoplasma spp.; swine enteric disease related to infection by *E. coli, Lawsonia intracellularis,* Salmonella, or *Serpulina hyodyisinteriae;* cow footrot related to infection by Fusobacterium spp.; cow metritis related to infection by *E. coli;* cow hairy warts related to infection by *Fusobacterium necrophorum* or *Bacteroides nodosus;* cow pink-eye related to infection by *Moraxella bovis;* cow premature abortion related to infection by protozoa (i.e. neosporium); urinary tract infection in dogs and cats related to infection by *E. coli;* skin and soft tissue infections in dogs and cats related to infection by *Staph. epidermidis, Staph. intermedius, coagulase neg.* Staph. or *P. multocida;* and dental or mouth infections in dogs and cats related to infection by Alcaligenes spp., Bacteroides spp., Clostridium spp., Enterobacter spp., Eubacterium, Peptostreptococcus, Porphyromonas, or Prevotella. Other bacterial infections and protozoa infections and disorders related to such infections that may be treated or prevented in accord with the method of the present invention are referred to in J. P. Sanford et al., "The Sanford Guide To Antimicrobial Therapy," 26th Edition, (Antimicrobial Therapy, Inc., 1996).

In the chemical structures depicted herein, a wavy line indicates that the stereochemistry at the chiral center to which the wavy line is connected is either an R or S configuration where the wavy line is connected to a carbon atom. In the compound of formula 3, the wavy line connected to the oxime nitrogen at position 9 of the macrolide ring indicates that the $-OR^z$ moiety is in an E or Z configuration.

The term "halo", as used herein, unless otherwise indicated, means fluoro, chloro, bromo or iodo. Preferred halo groups are fluoro, chloro and bromo.

The term "alkyl", as used herein, unless otherwise indicated, includes saturated monovalent hydrocarbon radicals having straight, cyclic or branched moieties. Said alkyl group may include one or two double or triple bonds. It is understood that for cyclic moieties at least three carbon atoms are required in said alkyl group.

The term "alkanoyl", as used herein, unless otherwise indicated, includes —C(O)-alkyl groups wherein "alkyl" is as defined above.

The term "aryl", as used herein, unless otherwise indicated, includes an organic radical derived from an aromatic hydrocarbon by removal of one hydrogen, such as phenyl or naphthyl.

As used herein, unless otherwise indicated, "Ac" indicates an acetyl group.

As used herein, unless otherwise indicated, "Me" indicates a methyl group.

The term "4-10 membered heterocyclic", as used herein, unless otherwise indicated, includes aromatic and non-aromatic heterocyclic groups containing one or more heteroatoms each selected from O, S and N, wherein each heterocyclic group has from 4–10 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems and ring systems substituted with one or more oxo moieties. An example of a 5 membered heterocyclic group is thiazolyl, and an example of a 10 membered heterocyclic group is quinolinyl. Examples of non-aromatic heterocyclic groups are pyrrolidinyl, piperidino, morpholino, thiomorpholino and piperazinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl and thiazolyl. In general, acceptable 4–10 membered heterocyclic groups include those derived from one of the following: furan, thiophene, 2H-pyrrole, pyrrole, 2-pyrroline, 3-pyrroline, pyrrolidine, 1,3-dioxolane, oxazole, thiazole, imidazole, 2-imidazole, imidazolidine, pyrazole, 2-pyrazoline, pyrazolidine, isoxazole, isothiazole, 1,2,3-oxadiazole, 1,2,3-triazole, 1,3,4-thiadiazole, 2H-pyran, 4H-pyran, pyridine, piperidine, 1,4-dioxane, 1,3-dioxane, morpholine, 1,4-dithiane, thiomorpholine, pyridazine, pyrimidine, pyrazine, piperazine, 1,3,5-triazine, 1,3,5-trithiane, indolizine, indole, isoindole, 3H-indole, indoline, benzofuran, benzothiophene, 1H-indazole, benzimidazole, benzthiazole, purine, 4H-quinolizine, quinoline, isoquinoline, cinnoline, phthalazine, quinazoline, quinoxaline, 1,8-naphthyridine, pteridine, quinuclidine, carbazole, acridine, phenazine, phenothiazine, phenoxazine, tetrazole, thietane and azetidine.

The phrase "pharmaceutically acceptable salt(s)", as used herein, unless otherwise indicated, includes salts of acidic or basic groups which may be present in the compounds of formula I-3. The compounds of formula I-3 that are basic in nature are capable of forming a wide variety of salts with various inorganic and organic acids. The acids that may be used to prepare pharmaceutically acceptable acid addition salts of such basic compounds of formula I are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate i.e., 1,1'-methylene-bis-(2-hydroxy-3-naphthoate)] salts.

Those compounds of the formula I3 that are acidic in nature, are capable of forming base salts with various pharmaceutically acceptable cations. Examples of such salts include the alkali metal or alkaline earth metal salts and particularly, the sodium and potassium salts.

The present invention also includes all radio-labeled forms of the compounds of formula 1–3, and pharmaceutically acceptable salts thereof, wherein the radio-label is selected from $^3H$, $^{11}C$ and $^{14}C$. Such radio-labeled compounds are useful as research or diagnostic tools.

Certain compounds of formula 1–3 may have asymmetric centers and therefore exist in different enantiomeric forms. This invention relates to the use of all optical isomers and stereoisomers of the compounds of formula 1 and mixtures thereof. In particular, the invention includes both the R and S configurations of C-2 and C-10 the macrolide ring of formula 1–3. The compounds of formula 1–3 may also exist as tautomers. This invention relates to the use of all such tautomers and mixtures thereof.

DETAILED DESCRIPTION OF THE INVENTION

The preparation of the compounds of the present invention is illustrated in the following Schemes 1 to 5.

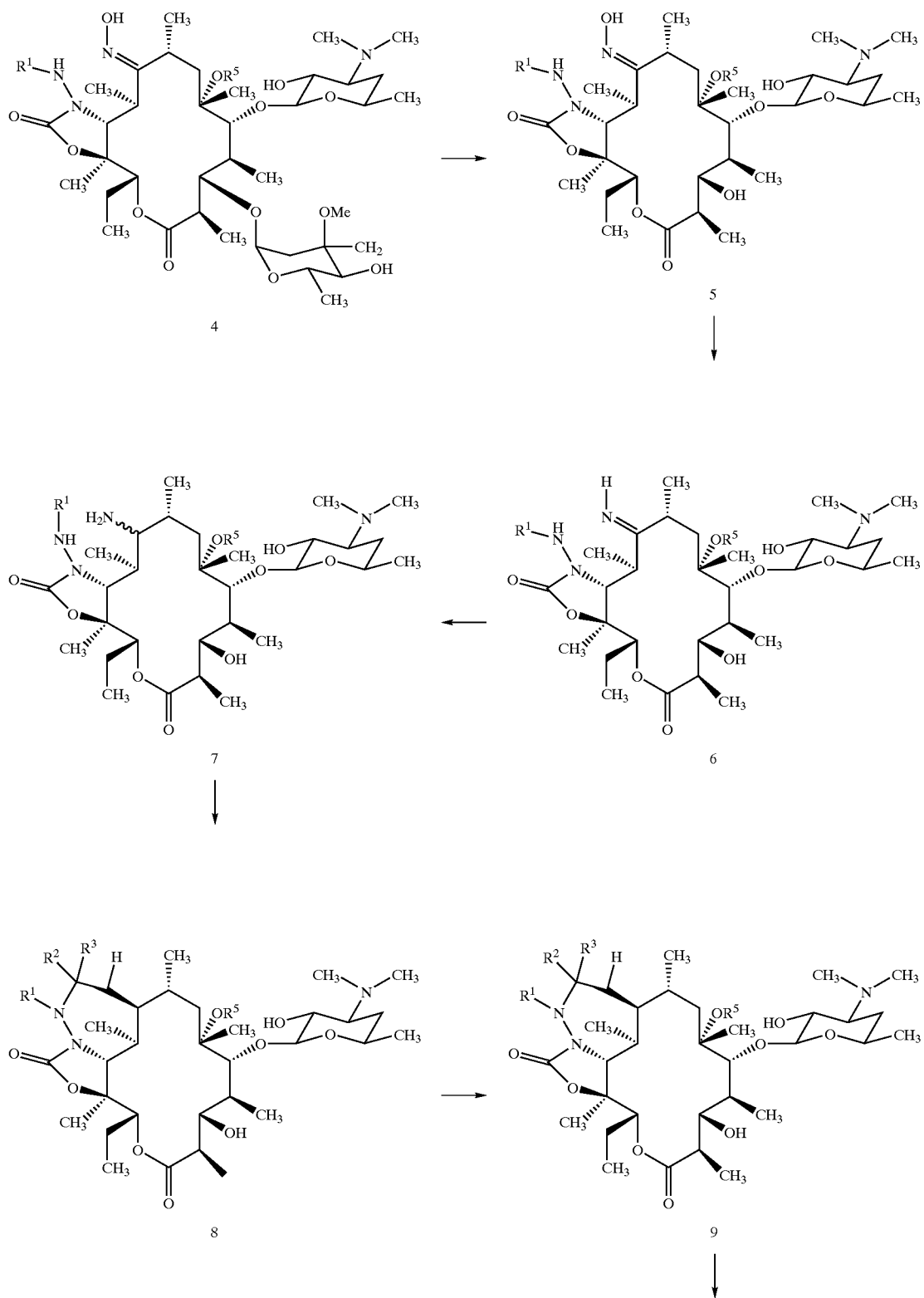
Scheme 1

-continued

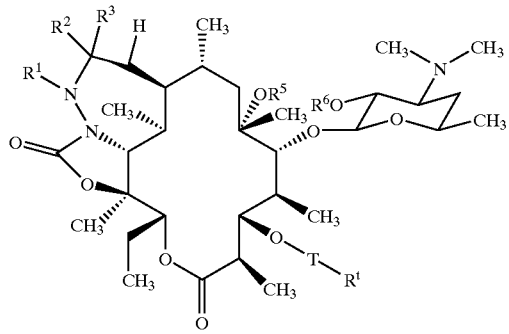

1

Scheme 1 depicts the general synthesis of compound of formula 1. The synthesis of compound 4 is disclosed in U.S. provisional patent application No. 60/106,798, filed Nov. 3, 1998, which is incorporated herein in its entirety by reference thereto. Exposure of compound 4 to acidic conditions can effect the cleavage of the cladinose sugar to give the compound of formula 5. The preferred acidic condition is HCl in ethanol. The reduction of 9-hydroxyimino group of the compound of formula 5 can be effected by treating the starting compound with a reducing agent such as $TiCl_3$ in a polar solvent such as methanol. The resulting imine of formula 6 can be converted to the corresponding amine of formula 7, by means of reduction with a reducing agent such as $NaBH_3CN$ in a polar solvent such as methanol. The conversion of the compound of formula 7 to formula 8 can be effected by following substantially the same procedures as described in PCT publication WO 9921865 (Pfizer. Inc., Yong-Jin Wu), to wit, by treatment of the compound of formula 7 with $R^2R^3C{=}O$ in the presence of an acid catalyst such as acetic acid to PTSA (p-toluenesulfonic acid), in a solvent such as ethanol or toluene, at a temperature within the range of 40 to 80 degrees C. for a period of 1 to 24 hours. Compounds of formula 8 can be converted to that of formula 9 through alkylation or reductive alkylation by methods known to one skilled in the art. Compounds of formula 1 can be prepared from compounds of formula 9 by many methods known to those skilled in the art.

Scheme 2

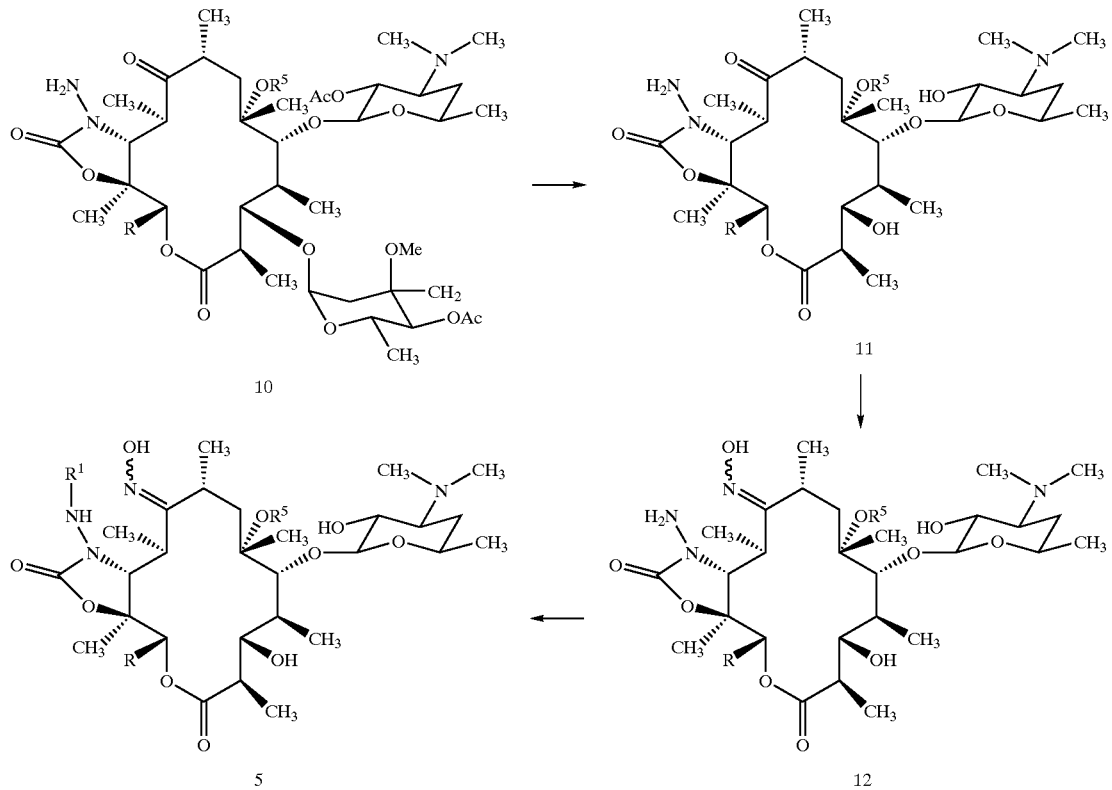

Scheme 2 describes an alternative synthesis of the compound of formula 5. The starting compound of formula 10 is disclosed in PCT publication WO97/31929. Compounds of formula 10 can be converted to that of formula 11 by treating the compound of formula 10 with acidic conditions followed by methanol. The preferred acidic condition is HCl in ethanol. Oximation of the compound of formula 11 can be carried out by methods known to those skilled in the art. The preferred oximation condition is hydroxylamine hydrochloride and pyridine in n-butanol at 70–90□C. The conversion of the compound of formula 12 to the compound of formula 5 can be effected by direct alkylation or reductive alkylation using methods known to one skilled in the art.

Scheme 3

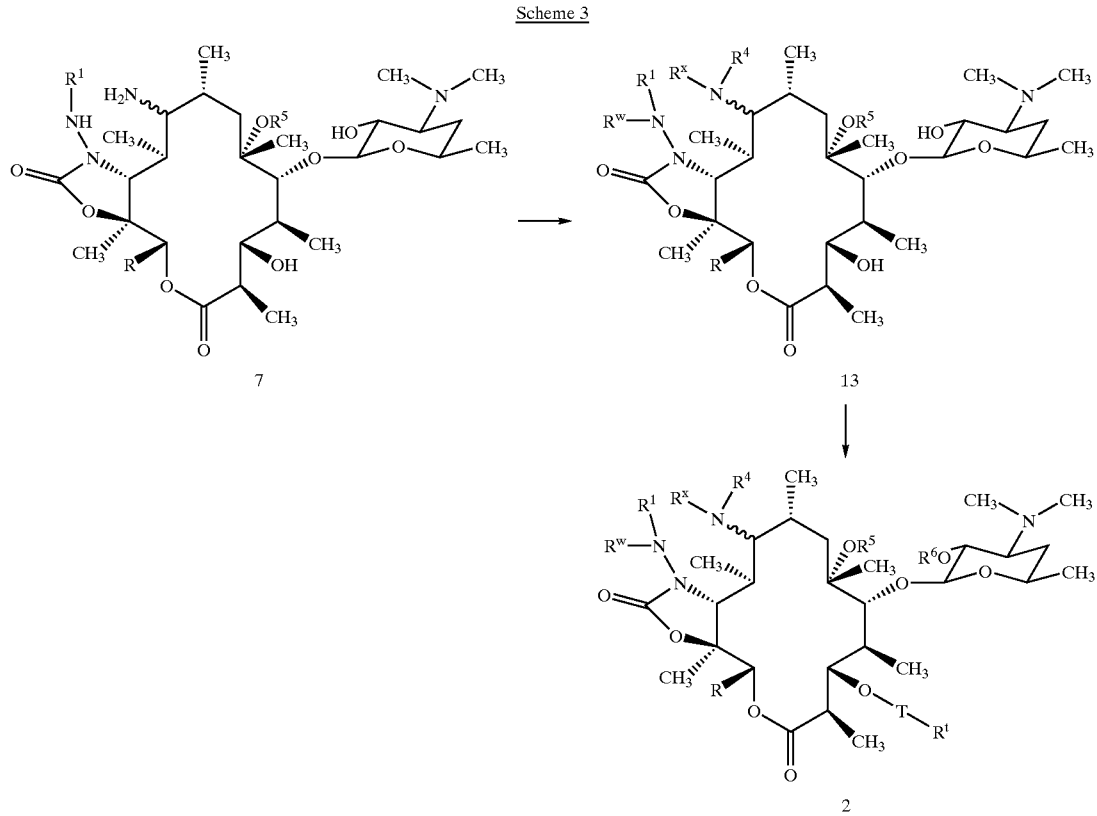

Scheme 3 describes a general synthesis of compounds of formula 2. The starting compound of formula 7 is available from Scheme 1. Compound 7 can be converted to 13 through reductive alkylation or direct alkylation by a variety of methods known to those skilled in the art. Compounds of formula 2 can be synthesized from those of 13 by many methods known to one skilled in the art.

Scheme 4

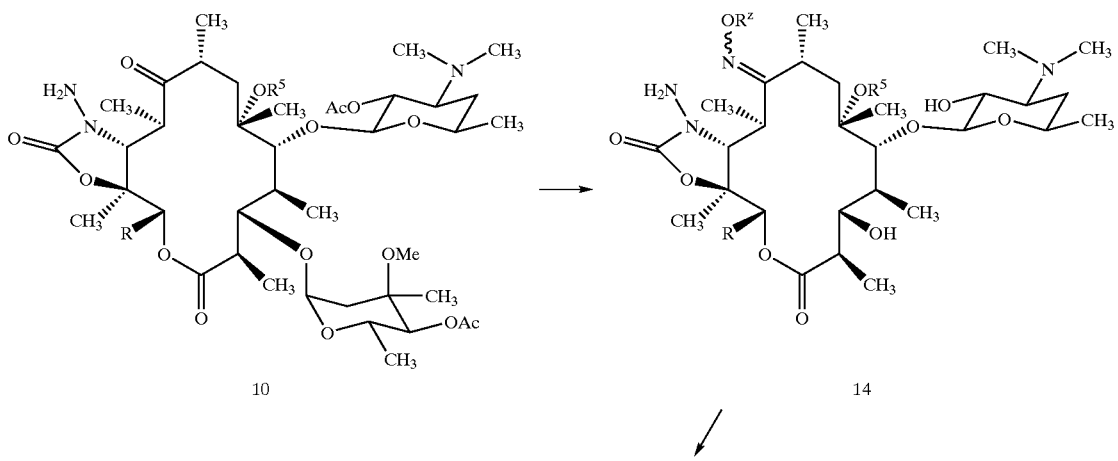

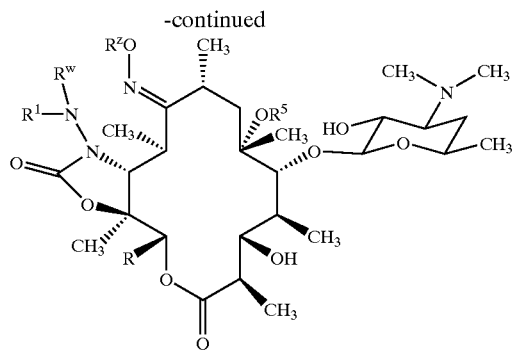

15

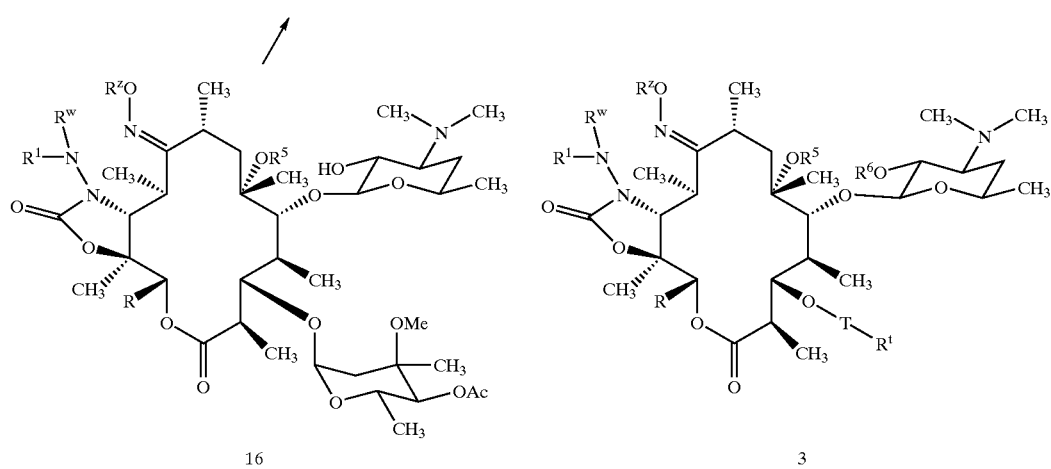

16    3

Scheme 4 depicts the general synthesis of compound of formula 3 wherein the starting compound of formula 10 is disclosed in PCT publication WO97/31929. Compounds of formula 14 can be synthesized from the compound of formula 10 by treatment with $R^zONH_2 \cdot HCl$ and base in a solvent, preferably at a temperature from 50 to 100° C. Preferred bases include, but are not limited to, triethylamine, 2,6-lutidine, 1,8-diazabicyclo95.4.0)undec-7-ene (DBU), and N,N-diethylpropylamine. Preferred solvents include, but are not limited to, acetonitrile, methanol, ethanol, and n-butanol. The conversion of the compound of formula 14 to the compound of formula 15 can be effected through alkylation or reduction alkylation using methods known to those skilled in the art. Alternatively, compounds of formula 15 can be derived from compounds of formula 16. The synthesis of compounds of formula 16 is disclosed in U.S. provisional patent application No. 60/106,798, filed Nov. 3, 1998, which is incorporated herein in its entirety by reference thereto. Compounds of formula 15 can be synthesized from compounds of formula 16 by treatment with $R^zONH_2 \cdot HCl$ and base in a solvent, preferably at a temperature from 50 to 100° C. Preferred bases include, but are not limited to, triethylamine, 2,6-lutidine, 1,8-diazabicyclo95.4.0)undec-7-ene (DBU), and N,N-diethylpropylamine. Preferred solvents include, but are not limited to, acetonitrile, methanol, ethanol, and n-butanol. The transformation from the compounds of formula 16 to compounds of formula 3 can be achieved by many methods known to one skilled in the art.

Scheme 5

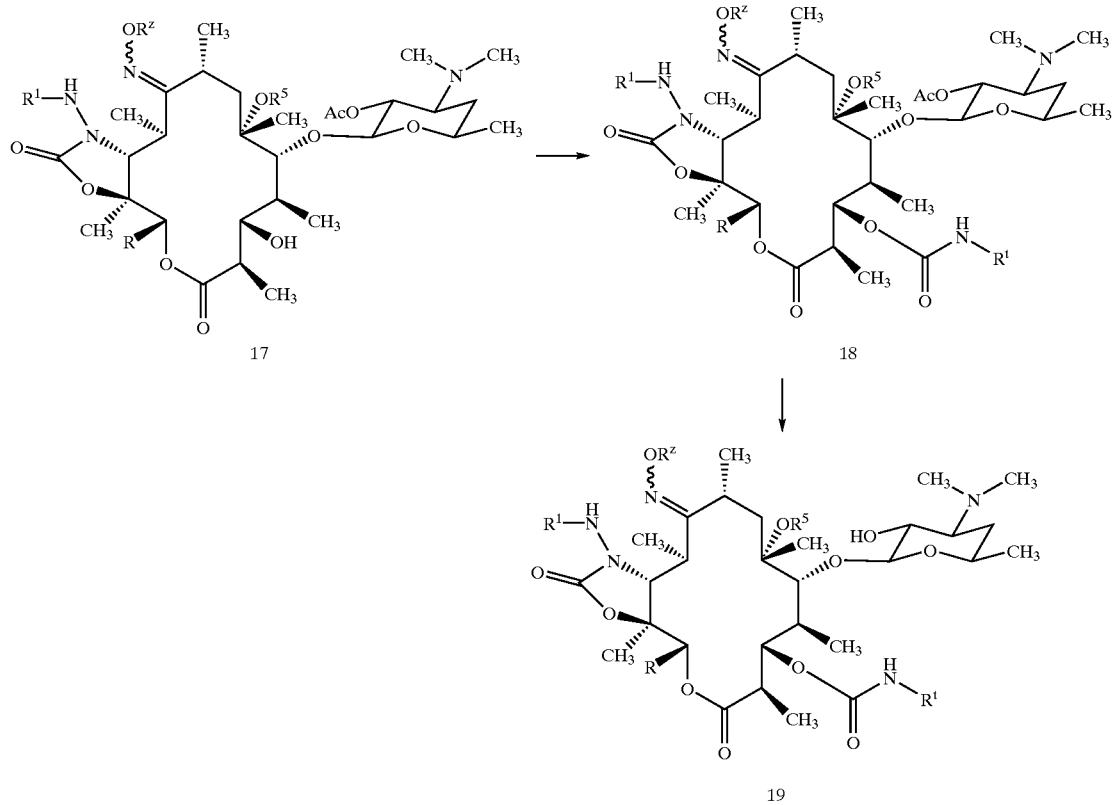

Scheme 5 describes the synthesis of a compound of formula 3, wherein $R^w$ is H, $R^6$ is H, T is —C(O)—NH—, as shown by the compound of formula 19. Compounds of formula 17 can be prepared from 15, wherein $R^w$ is hydrogen. Compounds of formula 18 can be prepared by treatment the compound of formula 17 with a compound of formula $R^t$—N=C=O in a solvent such as toluene in the presence of a base such as 4-dimethylaminopyridine (DMAP) at 30–110° C. The conversion of the compound of formula 18 to the compound of formula 19 can be effected by treatment with methanol at 50–70° C.

The compounds of the present invention may have asymmetric carbon atoms. Such diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers are considered as part of the invention.

The compounds of formula 1–3 that are basic in nature are capable of forming a wide variety of different salts with various inorganic and organic acids. Although such salts must be pharmaceutically acceptable for administration to animals, it is often desirable in practice to initially isolate the compound of formula I from the reaction mixture as a pharmaceutically unacceptable salt and then simply converting the latter back to the free base compound by treatment with an alkaline reagent and subsequently converting the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding an appropriate mineral or organic acid to the solution.

Those compounds of the formulas I-3 which are acidic in nature, are capable of forming base salts with various pharmacologically acceptable cations. Examples of such salts include the alkali metal or alkaline-earth metal salts and particularly, the sodium and potassium salts. These salts may be prepared by conventional techniques. The chemical bases which are used as reagents to prepare the pharmaceutically acceptable base salts of this invention are those which form non-toxic base salts with the acidic compounds of formula 1–3. Such non-toxic base salts include those derived from such pharmacologically acceptable cations as sodium, potassium calcium and magnesium, etc. These salts can be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before.

In either case, stoichiometric quantities of reagents are preferably employed in order to ensure completeness of reaction and maximum yields of the desired final product.

The activity of the compounds of the present invention against bacterial and protozoa pathogens is demonstrated by the compound's ability to inhibit growth of defined strains of human (Assay I) or animal (Assays II and III) pathogens.

Assay I

Assay I, described below, employs conventional methodology and interpretation criteria and is designed to provide direction for chemical modifications that may lead to compounds that circumvent defined mechanisms of macrolide resistance. In Assay I, a panel of bacterial strains is assembled to include a variety of target pathogenic species, including representatives of macrolide resistance mechanisms that have been characterized. Use of this panel enables the chemical structure/activity relationship to be determined with respect to potency, spectrum of activity, and structural elements or modifications that may be necessary to obviate resistance mechanisms. Bacterial pathogens that comprise the screening panel are shown in the table below. In many cases, both the macrolide-susceptible parent strain and the macrolide-resistant strain derived from it are available to provide a more accurate assessment of the compound's ability to circumvent the resistance mechanism. Strains that contain the gene with the designation of ermA/ermB/ermC are resistant to macrolides, lincosamides, and streptogramin B antibiotics due to modifications (methylation) of 23S rRNA molecules by an Erm methylase, thereby generally preventing the binding of all three structural classes. Two types of macrolide efflux have been described; msrA encodes a component of an efflux system in staphylococci that prevents the entry of macrolides and streptogramins while mefA/E encodes a transmembrane protein that appears to efflux only macrolides. Inactivation of macrolide antibiotics can occur and can be mediated by either a phosphorylation of the 2'-hydroxyl (mph) or by cleavage of the macrocyclic lactone (esterase). The strains may be characterized using conventional polymerase chain reaction (PCR) technology and/or by sequencing the resistance determinant. The use of PCR technology in this application is described in J. Sutcliffe et al., "Detection Of Erythromycin-Resistant Determinants By PCR", Antimicrobial Agents and Chemotherapy, 40(11), 2562–2566 (1996). The antibacterial assay is performed in microtiter trays and interpreted according to *Performance Standards for Antimicrobial Disk Susceptibility Tests—Sixth Edition*; Approved Standard, published by The National Committee for Clinical Laboratory Standards (NCCLS) guidelines; the minimum inhibitory concentration (MIC) is used to compare strains. acr AB or acr AB-like indicates that an intrinsia multidrug efflux pump exists in the strain. Compounds are initially dissolved in dimethylsulfoxide (DMSO) as 40 mg/ml stock solutions.

| Strain Designation | Macrolide Resistance Mechanism(s) |
| --- | --- |
| *Staphylococcus aureus* 1116 | susceptible parent |
| *Staphylococcus aureus* 1117 | ermB |
| *Staphylococcus aureus* 0052 | susceptible parent |
| *Staphylococcus aureus* 1120 | ermC |
| *Staphylococcus aureus* 1032 | msrA, mph, esterase |
| *Staphylococcus hemolyticus* 1006 | msrA, mph |
| *Streptococcus pyogenes* 0203 | susceptible parent |
| *Streptococcus pyogenes* 1079 | ermB |
| *Streptococcus pyogenes* 1062 | susceptible parent |
| *Streptococcus pyogenes* 1061 | ermB |
| *Streptococcus pyogenes* 1064 | mefA |
| *Streptococcus agalactiae* 1024 | susceptible parent |
| *Streptococcus agalactiae* 1023 | ermB |
| *Streptococcus pneumoniae* 1016 | susceptible |
| *Streptococcus pneumoniae* 1046 | ermB |
| *Streptococcus pneumoniae* 1095 | ermB |
| *Streptococcus pneumoniae* 1175 | mefE |
| *Haemophilus influenzae* 0085 | susceptible; acr AB-like |
| *Haemophilus influenzae* 0131 | susceptible; acr AB-like |
| *Moraxella catarrhalis* 0040 | susceptible |
| *Moraxella catarrhalis* 1055 | erythromycin intermediate resistance |
| *Escherichia coli* 0266 | susceptible; acr AB |
| *Haemophilus influenzae* 1100 | susceptible; acr AB-like |

Assay II is utilized to test for activity against *Pasteurella multocida* and Assay III is utilized to test for activity against *Pasteurella haemolytica*.

Assay II

This assay is based on the liquid dilution method in microliter format. A single colony of *P. multocida* (strain 59A067) is inoculated into 5 ml of brain heart infusion (BHI) broth. The test compounds are prepared by solubilizing 1 mg of the compound in 125 $\mu$l of dimethylsulfoxide (DMSO). Dilutions of the test compound are prepared using uninoculated BHI broth. The concentrations of the test compound used range from 200 $\mu$g/ml to 0.098 $\mu$g/ml by two-fold serial dilutions. The *P. multocida* inoculated BHI is diluted with uninoculated BHI broth to make a $10^4$ cell suspension per 200 $\mu$l. The BHI cell suspensions are mixed with respective serial dilutions of the test compound, and incubated at 37° C. for 18 hours. The minimum inhibitory concentration (MIC) is equal to the concentration of the compound exhibiting 100% inhibition of growth of *P. multocida* as determined by comparison with an uninoculated control.

Assay III

This assay is based on the agar dilution method using a Steers Replicator. Two to five colonies isolated from an agar plate are inoculated into BHI broth and incubated overnight at 37° C. with shaking (200 rpm). The next morning, 300 $\mu$l of the fully grown *P. haemolytica* preculture is inoculated into 3 ml of fresh BHI broth and is incubated at 37° C. with shaking (200 rpm). The appropriate amounts of the test compounds are dissolved in ethanol and a series of two-fold serial dilutions are prepared. Two ml of the respective serial dilution is mixed with 18 ml of molten BHI agar and solidified. When the inoculated *P. haemolytica* culture reaches 0.5 McFarland standard density, about 5 $\mu$l of the *P. haemolytica* culture is inoculated onto BHI agar plates containing the various concentrations of the test compound using a Steers Replicator and incubated for 18 hours at 37° C. Initial concentrations of the test compound range from 100–200 $\mu$g/ml. The MIC is equal to the concentration of the test compound exhibiting 100% inhibition of growth of *P. haemolytica* as determined by comparison with an uninoculated control.

The in vivo activity of the compounds of formula (I) can be determined by conventional animal protection studies well known to those skilled in the art, usually carried out in mice.

Mice are allotted to cages (10 per cage) upon their arrival, and allowed to acclimate for a minimum of 48 hours before being used. Animals are inoculated with 0.5 ml of a $3\times10^3$ CFU/ml bacterial suspension (*P. multocida* strain 59A006) intraperitoneally. Each experiment has at least 3 non-medicated control groups including one infected with 0.1× challenge dose and two infected with 1×challenge dose; a 10×challenge data group may also be used. Generally, all mice in a given study can be challenged within 30–90 minutes, especially if a repeating syringe (such as a Cornwall® syringe) is used to administer the challenge. Thirty minutes after challenging has begun, the first compound treatment is given. It may be necessary for a second person to begin compound dosing if all of the animals have not been challenged at the end of 30 minutes. The routes of administration are subcutaneous or oral doses. Subcutaneous doses are administered into the loose skin in the back of the neck whereas oral doses are given by means of a feeding needle. In both cases, a volume of 0.2 ml is used per mouse. Compounds are administered 30 minutes, 4 hours, and 24 hours after challenge. A control compound of known efficacy administered by the same route is included in each test. Animals are observed daily, and the number of survivors in each group is recorded. The *P. multocida* model monitoring continues for 96 hours (four days) post challenge.

The $PD_{50}$ is a calculated dose at which the compound tested protects 50% of a group of mice from mortality due to the bacterial infection which would be lethal in the absence of drug treatment.

The compounds of formula 1–3 and their pharmaceutically acceptable salts or prodrugs (hereinafter referred to, collectively, as "the active compounds of this invention") may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining the active compounds of this invention can then be readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions containing an active compound of this invention or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

To implement the methods of this invention, an effective dose of an active compound of this invention is administered to a susceptible or infected animal (including mammals, fish and birds) by parenteral (i.v., i.m. or s.c.), oral, or rectal routes, or locally as a topical application to the skin and/or mucous membranes. The route of administration will depend on the mammal, fish or bird that is being treated. The effective dose will vary with the severity of the disease, and the age, weight and condition of the animal. However, the daily dose will usually range from about 0.25 to about 150 mg/kg body weight of the patient to be treated, preferably from about 0.25 to about 25 mg/kg.

The Examples provided below illustrate specific embodiments of the invention, but the invention is not limited in scope to the Examples specifically exemplified.

EXAMPLE 1

Compound of formula 1, wherein R=Et, $R^5$=Me, $R^1$=3-(4-pyridin-3-yl-imidazol)-propyl, $R^2$=$R^3$=$R^4$=$R^6$=H, T is absent, $R^t$=H 37% aqueous formaldehyde (0.2 mL) was added to a solution of a compound of formula 7, (wherein $R^5$=Me, $R^1$=3-(4-pyridin-3-yl-imidazol)-propyl (1.97 g), obtained as above), in methanol (24 mL) and the resulting solution was stirred at room temperature for 1.5 h. Saturated $NaHCO_3$ was added, most of the solvent was removed in vacuo, and the aqueous layer was extracted with $CH_2Cl_2$ (×3). The combined organic layers were washed with brine, dried over anhydrous $MgSO_4$, and concentrated in vacuo to afford the title compound.

MS: m/z 829 (M+H).

EXAMPLE 2

Compound of formula 3, wherein R=Et, $R^5$=$R^z$=Me, $R^w$=H, $R^1$=3-(4-pyridin-3-yl-imidazol)-propyl, T is —C(O)—NH—, $R^t$=n-propyl To a solution of compound of formula 13 (200mg), wherein $R^5$=$R^z$=Me, $R^1$=3-(4-pyridin-3-yl-imidazol)-propyl, in toluene (3 mL) was added 4-dimethylaminopyridine (28 mg) and n-propyl isocyanate (0.28 mL), and the resulting solution was heated at 90□C. 5 h. The reaction mixture was cooled to room temperature, and methanol (6 mL) was added. The solution was heated at 70□C. for 12 h. The solvents were removed in vacuo, and the residue was purified by preparative TLC (89% $CH_2Cl_2$-10% MeOH-1% $NH_3$□□□$_2$O) to afford the title compound as a white solid.

MS: m/z 930 (M+H).

EXAMPLE 3

Compound of formula 3, wherein R=Et, $R^5$=$R^z$=Me, $R^w$=H, $R^1$=3-(4-pyridin-3-yl-imidazol)-propyl, T is —C(O)—NH—, $R^t$=iso-propyl To a solution of compound of formula 13 (200 mg), wherein $R^5$=$R^z$=Me, $R^1$=3-(4-pyridin-3-yl-imidazol)-propyl, in toluene (3 mL) was added 4-dimethylaminopyridine (28 mg) and iso-propyl isocyanate (0.29 mL), and the resulting solution was heated at 90°C. 5 h. The reaction mixture was cooled to room temperature, and methanol (6 mL) was added. The solution was heated at 70°C. for 12 h. The solvents were removed in vacuo, and the residue was purified by preparative TLC (89% $CH_2Cl_2$-10% MeOH-1% $NH_3$□□□$_2$O) to afford the title compound as a white solid.

MS: m/z 930 (M+H).

EXAMPLE 4

Compound of formula 3, wherein R=Et, $R^5$=$R^z$=Me, $R^w$=H, $R^1$=3-(4-pyridin-3-yl-imidazol)-propyl, T is —C(O)—NH—, R'=4-fluorophenyl To a solution of compound of formula 13 (200 mg), wherein $R^5$=$R^z$=Me, $R^1$=3-(4-pyridin-3-yl-imidazol)-propyl, in toluene (3 mL) was added 4-dimethylaminopyridine (28 mg) and 4-fluorophenyl isocyanate (0.33 mL), and the resulting solution was heated at 90°C. 10 h. The reaction mixture was cooled to room temperature, and methanol (6 mL) was added. The solution was heated at 70°C. for 12 h. The solvents were removed in vacuo, and the residue was purified by preparative TLC (89% $CH_2Cl_2$-10% MeOH-1% $NH_3$□□□$_2$O) to afford the title compound as a white solid.

MS: m/z 982 (M+H).

EXAMPLE 5

Compound of formula 3, wherein R=Et, $R^5$=$R^z$=Me, $R^w$=H, $R^1$=3-(4-pyridin-3-yl-imidazol)-propyl, T is —C(O)—NH—, R'=phenyl To a solution of compound of formula 13 (200 mg), wherein $R^5$=$R^z$=Me, $R^1$=3-(4-pyridin-3-yl-imidazol)-propyl, in toluene (3 mL) was added 4-dimethylaminopyridine (28 mg) and phenyl isocyanate (0.32 mL), and the resulting solution was heated at 90°C. 10 h. The reaction mixture was cooled to room temperature, and methanol (6 mL) was added. The solution was heated at 70°C. for 12 h. The solvents were removed in vacuo, and the residue was purified by preparative TLC (89% $CH_2Cl_2$-10% MeOH-1% $NH_3$□□□$_2$O) to afford the title compound as a white solid.

MS: m/z 964 (M+H).

EXAMPLE 6

Compound of formula 3, wherein R=Et, $R^5$=$R^z$=Me, $R^w$=H, $R^1$=3-(4-pyridin-3-yl-imidazol)-propyl, T is —C(O)—NH—, R'=allyl To a solution of compound of formula 13 (200 mg), wherein $R^5$=$R^z$=Me, $R^1$=3-(4-pyridin-3-yl-imidazol)-propyl, in toluene (3 mL) was added 4-dimethylaminopyridine (28 mg) and allyl isocyanate (0.24 mL), and the resulting solution was heated at 90°C. 10 h. The reaction mixture was cooled to room temperature, and methanol (6 mL) was added. The solution was heated at 70°C. for 12 h. The solvents were removed in vacuo, and the residue was purified by preparative TLC (89% $CH_2Cl_2$-10% MeOH-1% $NH_3$□□□$_2$O) to afford the title compound as a white solid.

MS: m/z 928 (M+H).

EXAMPLE 7

Compound of formula 5, wherein R=Et, $R^5$=Me, $R^1$=3-(4-pyridin-3-yl-imidazol)-propyl To a solution of compound 12, wherein $R^5$ is Me, (6.36 g, 9.86 mmol) in toluene (100 mL) was added 3-(4-pyridin-3-yl-imidazol)-propionaldehyde (3.34 g), and the resulting solution was heated at 60°C. for 20 h. Toluene was removed, and the residue was dried in vacuo. This residue was dissolved in methanol (100 mL), and acetic acid (8.5 mL) and $NaBH_3CN$ (6.2 g) were added. The resulting solution was stirred at room temperature for 5 h. Sat. $NaHCO_3$ was added, most solvent was removed in vacuo, and the aqueous layer was extracted with $CH_2Cl_2$ (×3). The combined organic layers were washed with brine, dried over anhydrous $MgSO_4$, and concentrated in vacuo to afford the title compound as an off-white solid (5.6 g).

MS: m/z 831 (M+H).

EXAMPLE 8

Compound of formula 6, wherein R=Et, $R^5$=Me, $R^1$=3-(4-pyridin-3-yl-imidazol)-propyl $TiCl_3$ (0.66M in HCl) was added to a suspension of compound 5, wherein $R^5$=Me, $R^1$=3-(4-pyridin-3-yl-imidazol)-propyl (5.6 g, 9.86 mmol) and $NH_4OAc$ (11.1 g) in methanol (65 mL) at room temperature. The resulting reaction mixture was stirred at room temperature for 2 h. Sat. $NaHCO_3$ was added, most solvent was removed in vacuo, and the aqueous layer was extracted with $CH_2Cl_2$ (×3). The combined organic layers were washed with brine, dried over anhydrous $MgSO_4$, and concentrated in vacuo to afford the title compound.

MS: m/z 815 (M+H).

EXAMPLE 9

Compound of formula 7, wherein R=Et, $R^5$=Me, $R^1$=3-(4-pyridin-3-yl-imidazol)-propyl $NaBH_3CN$ (6.3 g) was added to a solution of compound 6, wherein $R^5$=Me, $R^1$=3-(4-pyridin-3-yl-imidazol)-propyl obtained as above, in acetic acid (5.8 mL) and methanol (65 mL) at room temperature. The resulting reaction mixture was stirred at room temperature for 12 h. Sat. $NaHCO_3$ was added, most solvent was removed in vacuo, and the aqueous layer was extracted with $CH_2Cl_2$ (×3). The combined organic layers were washed with brine, dried over anhydrous $MgSO_4$, and concentrated in vacuo to afford the title compound.

MS: m/z 817 (M+H).

EXAMPLE 10

Compound of formula 11, wherein R=Et, $R^5$=Me

Acetyl chloride (24.3 mL, 0.34 mol) was added dropwise to ethanol (145 mL) in an ice bath over a period of 15 min. The solution was stirred in an ice bath for 15min and then added to a solution of compound of formula 10, wherein $R^5$ is Me (99.2 g, 0.11 mol) in ethanol (295 mL). The resulting solution was stirred at room temperature for 12 h. Sat. $NaHCO_3$ was added, and most ethanol was removed in vacuo. The residue was extracted with $CH_2Cl_2$ (×4). The combined organics were washed with $H_2O$ and brine, dried over anhydrous $Na_2SO_4$, and concentrated in vacuo. The crude product was stirred in iso-propylether, the slurry was then filtered off, the solid was washed with iso-propylether. The washed solid was dissolved in methanol and stirred at 80°C. for 2 h. Methanol was removed in vacuo to afford the title compound as a off-white powder.

MS: m/z 630 (M+H).

EXAMPLE 11

Compound of formula 12, wherein R=Et, $R^5$=Me

To a solution of compound of formula 11, wherein $R^5$ is Me, (9.8 g, 15.6 mmol) in n-butanol (10 mL) was added hydroxylamine hydrochloride (10.8 g, 156 mmol) and pyridine (12.6 mL, 156 mmol), and the resulting solution was heated at 80°C. for 5 days. Sat. NaHCO$_3$ was added, and most solvent was removed in vacuo. The residue was extracted with ethyl acetate (×4). The combined organics were washed with H$_2$O and brine, dried over anhydrous Na$_2$SO$_4$, and concentrated in vacuo to afford the title compound as white solid (6.4 g).

MS: m/z 645 (M+H).

What is claimed is:

1. A compound of the formula I or pharmaceutically acceptable salts or prodrugs thereof, wherein:

R is $C_1$–$C_{10}$ alkyl, $C_3$–$C_{10}$ alkenyl, $C_3$–$C_{10}$ alkynyl, or $C_3$–$C_{10}$ cycloalkyl, wherein one or two carbons of said alkyl, cycloalkyl, alkenyl, alkynyl are optionally replaced by one or more heteroatoms selected from O, S and N, and are optionally substituted by one or more substituents selected from the group (hereinafter also referred to as "Group A") consisting of:

nitro;
N$_3$;
CN;
$C_1$–$C_{10}$ alkoxy;
$C_1$–$C_{10}$ alkanoyl;
$C_1$–$C_{10}$ alkyl;
$C_2$–$C_{10}$ alkenyl;
$C_2$–$C_{10}$ alkynyl;
$C_3$–$C_{10}$ cycloalkyl;
4 to 10 heterocyclic;
—C(O)R$^{10}$;
—C(O)OR$^{10}$;
—NR$^{10}$R$^{11}$;
—NHC(O)R$^{10}$;
—NHC(O)NR$^{10}$R$^{11}$;
—S(O)$_n$, wherein n is 0, 1, or 2;
—SO$_2$R$^{10}$;
—SO$_2$NR$^{10}$R$^{11}$;

wherein each R$^1$, R$^2$, R$^3{}_1$, and R$^4$ is independently selected from the group consisting of H, $C_1$–$C_{12}$ alkyl, $C_3$–$C_{10}$ alkenyl, $C_3$–$C_{10}$ alkynyl, (CR$^8$R$^9$)$_m$Z, m is an integer from 0 to 6; wherein one or two carbons of said alkyl, alkenyl, alkynyl are optionally replaced by a heteroatom selected from the group consisting of O, S and N, and are optionally substituted by one or more substituents selected from Group A; or R$^2$ and R$^3$, together with the carbon to which they are attached, form a 3–10 membered ring; the ring carbons are optionally substituted by one or more heteroatoms selected from the group consisting of O, S and N;

R$^5$ is selected from the group consisting of $C_1$–$C_{10}$ alkyl, $C_3$–$C_{10}$ alkenyl, $C_3$–$C_{10}$ alkynyl, —CH$_2$—CH=CH—

Z, (CR$^9$R$^{10}$)$_m$Z; m is an integer from 1 to 6; wherein the alkyl, alkenyl and alkynyl can be substituted with one or more substituents selected from Group A;

R$^6$ is H, —C(O)O($C_1$–$C_{18}$) alkyl or —C(O)($C_1$–$C_{18}$) alkyl, wherein one or more carbons of said alkyl may be replaced by a heteroatom selected from O, S and N;

R$^8$ and R$^9$ are independently selected from the group consisting of H, halo, $C_1$–$C_6$ alkyl; or R$^8$ and R$^9$, together with the carbon to which they are attached, form a 3 to 10 membered cyclic or heterocyclic di-radical;

each R$^{10}$ and R$^{11}$ is individually H or $C_1$–$C_{12}$ alkyl, or aryl substituted $C_1$–$C_{12}$ alkyl, or heteroaryl substituted $C_1$–$C_{12}$ alkyl, wherein one or more carbons of either of said alkyl are optionally replaced by a heteroatom selected from O, S and N;

each Z is independently a 4–10 membered heterocyclic or $C_6$–$C_{10}$ aryl, wherein said heterocyclic and aryl groups are optionally substituted by one or more substituents selected from Group A;

T is absent or selected from the group consisting of:
—C(O)—,
—C(O)—O—,
—CH$_2$—,
—C(S)—S—,
—C(O)—NR$^{10}$—;
—S(O)$_n$—, where n is 0, 1, or 2,
—S(O)$_n$—O—, wherein n is 0, 1, or 2,
—P(O)(OR$^{10}$)$_n$—, n is 0, 1, or 2, and
—S(O)$_2$—NR$^{10}$—, R$^t$ is selected from the group consisting of: $C_1$–$C_6$ alkyl, $C_3$–$C_6$ alkenyl, $C_3$–$C_{12}$ cycloalkyl, aryl, heteroaryl, heterocycloalkyl, wherein said alkyl, alkenyl, cycloalkyl, aryl, heteroaryl, and heterocycloalkyl groups are optionally substituted by one or more substituents selected from Group A.

2. A compound of formula 2 or pharmaceutically acceptable salts or prodrugs thereof, wherein:

R is $C_1$–$C_{10}$ alkyl, $C_3$–$C_{10}$ alkenyl, $C_3$–$C_{10}$ alkynyl, or $C_3$–$C_{10}$ cycloalkyl, wherein one or two carbons of said alkyl, cycloalkyl, alkenyl, alkynyl are optionally replaced by one or more heteroatoms selected from the group consisting of O, S and N, and are optionally substituted by one or more substituents selected from the group (hereinafter also referred to as "Group A") consisting of:

nitro;
N$_3$;
CN;
$C_1$–$C_{10}$ alkoxy;

$C_1$–$C_{10}$ alkanoyl;
$C_1$–$C_{10}$ alkyl;
$C_2$–$C_{10}$ alkenyl;
$C_2$–$C_{10}$ alkynyl;
$C_3$–$C_{10}$ cycloalkyl;
$C_3$–$C_{10}$ heterocyclic;
—C(O)$R^{10}$;
—C(O)O$R^{10}$;
—N$R^{10}R^{11}$;
—NHC(O)$R^{10}$;
—NHC(O)N$R^{10}R^{11}$;
—S(O)$_n$, wherein n is 0, 1, or 2;
—SO$_2R^{10}$;
—SO$_2$N$R^{10}R^{11}$;

$R^1$ and $R^4$ are independently selected from H, $C_1$–$C_{12}$ alkyl, $C_3$–$C_{10}$ alkenyl, $C_3$–$C_{10}$ alkynyl, $(CR^8R^9)_mZ$, m is an integer from 0 to 6; wherein one or two carbons of said alkyl, alkenyl, alkynyl are optionally replaced by a heteroatom selected from O, S and N, and are optionally substituted by one or more substituents selected from Group A;

$R^5$ is selected from the group consisting of $C_1$–$C_{10}$ alkyl, $C_3$–$C_{10}$ alkenyl, $C_3$–$C_{10}$ alkynyl, —CH$_2$—CH=CH—Z, —$(CR^9R^{10})_mZ$; m is an integer from 1 to 6; wherein the alkyl, alkenyl and alkynyl can be substituted with one or more substituents selected from Group A;

$R^6$ is H, —C(O)O($C_1$–$C_{18}$) alkyl or —C(O)($C_1$–$C_{18}$) alkyl, wherein one or more carbons of said alkyl may be replaced by a heteroatom selected from O, S and N;

$R^8$ and $R^9$ are independently selected from H, halo, $C_1$–$C_6$ alkyl; or $R^8$ and $R^9$, together with the carbon to which they are attached, form a 3 to 10 membered cyclic or heterocyclic di-radical;

$R^{10}$ and $R^{11}$ are each independently H or $C_1$–$C_{12}$ alkyl, or aryl substituted $C_1$–$C_{12}$ alkyl, or heteroaryl substituted $C_1$–$C_{12}$ alkyl, wherein one or more carbons of said alkyl are optionally replaced by a heteroatom selected from O, S and N;

each Z is independently a 4–10 membered heterocyclic or $C_6$–$C_{10}$ aryl, wherein said heterocyclic and aryl groups are optionally substituted by one or more substituents selected from Group A;

T is absent or selected from the group consisting of:
—C(O)—,
—C(O)—O—,
—CH$_2$—,
—C(S)—S—,
—C(O)—N$R^{10}$—;
—S(O)$_n$—, where n is 0, 1, or 2
—S(O)$_n$—O—, wherein n is 0, 1, or 2,
—P(O)(O$R^{10}$)$_n$—, n is 0, 1, or 2, and
—S(O)$_2$—N$R^{10}$—, $R^t$ is selected from the group consisting of: $C_1$–$C_6$ alkyl, $C_3$–$C_6$ alkenyl, $C_3$–$C_{12}$ cycloalkyl, aryl, heteroaryl, heterocycloalkyl, wherein said alkyl, alkenyl, cycloalkyl, aryl, heteroaryl, and heterocycloalkyl groups are optionally substituted by one or more substituents selected from Group A;

$R^w$ and $R^x$ are each independently H, $C_1$–$C_{10}$ alkyl, $C_3$–$C_{10}$ alkenyl, $C_3$–$C_{10}$ alkynyl, $C_3$–$C_{10}$ cycloalkyl, wherein one or two carbons of said alkyl, cycloalkyl, alkenyl, alkynyl are optionally replaced by one or more heteroatoms selected from O, S and N. and are optionally substituted by one or more substituents selected from Group A.

3. A compound of formula 3

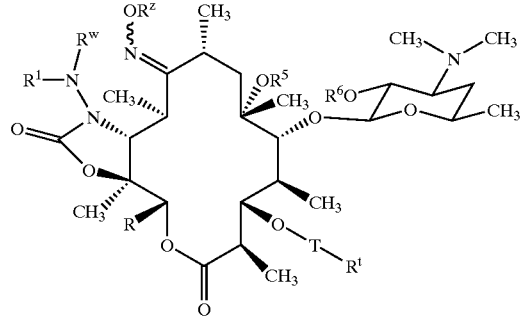

or pharmaceutically acceptable salts or prodrugs thereof, wherein:

R is $C_1$–$C_{10}$ alkyl, $C_3$–$C_{10}$ alkenyl, $C_3$–$C_{10}$ alkynyl, or $C_3$–$C_{10}$ cycloalkyl, wherein one or two carbons of said alkyl, cycloalkyl, alkenyl, and alkynyl are optionally replaced by one or more heteroatoms selected from the group consisting of O, S and N, and are optionally substituted by one or more substituents selected from the group (hereinafter also referred to as "Group A") consisting of:
nitro;
$N_3$;
CN;
$C_1$–$C_{10}$ alkoxy;
$C_1$–$C_{10}$ alkanoyl;
$C_1$–$C_{10}$ alkyl;
$C_2$–$C_{10}$ alkenyl;
$C_2$–$C_{10}$ alkynyl;
$C_3$–$C_{10}$ cycloalkyl;
$C_3$–$C_{10}$ heterocyclic;
—C(O)$R^{10}$;
—C(O)O$R^{10}$;
—N$R^{10}R^{11}$;
—NHC(O)$R^{10}$;
—NHC(O)N$R^{10}R^{11}$;
—S(O)$_n$, wherein n is 0, 1, or 2;
—SO$_2R^{10}$;
—SO$_2$N$R^{10}R^{11}$;

$R^1$ is selected from the group consisting of H, $C_1$–$C_{12}$ alkyl, $C_3$–$C_{10}$ alkenyl, $C_3$–$C_{10}$ alkynyl, and —$(CR^8R^9)_mZ$, m is an integer from 0 to 6; wherein one or two carbons of said alkyl, alkenyl, alkynyl are optionally replaced by a heteroatom selected from the group consisting of O, S and N, and are optionally substituted by one or more substituents selected from Group A;

$R^5$ is selected from the group consisting of $C_1$–$C_{10}$ alkyl, $C_3$–$C_{10}$ alkenyl, $C_3$–$C_{10}$ alkynyl, —CH$_2$—CH=CH—Z, and —$(CR^9R^{10})_mZ$; m is an integer from 1 to 6; wherein the alkyl, alkenyl and alkynyl can be substituted with one or more substituents selected from Group A;

$R^6$ is H, —C(O)O($C_1$–$C_{18}$) alkyl or —C(O)($C_1$–$C_{18}$) alkyl, wherein one or more carbons of said alkyl may be replaced by a heteroatom selected from O, S and N;

$R^8$ and $R^9$ are each independently selected from the group consisting of H, halo, $C_1$–$C_6$ alkyl; or $R^8$ and $R^9$, together with the carbon to which they are attached, form a 3 to 10 membered cyclic or heterocyclic di-radical;

$R^{10}$ and $R^{11}$ are each independently H or $C_1$–$C_{12}$ alkyl, or aryl substituted $C_1$–$C_{12}$ alkyl, or heteroaryl substituted $C_1$–$C_{12}$ alkyl, wherein one or more carbons of said alkyl are optionally replaced by a heteroatom selected from O, S and N;

each Z is independently a 4–10 membered heterocyclic or $C_6$–$C_{10}$ aryl, wherein said heterocyclic and aryl groups are optionally substituted by one or more substituents selected from Group A;

T is absent or selected from the group consisting of:
—C(O)—,
—C(O)—O—,
—$CH_2$—,
—C(S)—S—,
—C(O)—$NR^{10}$—;
—S(O)$_n$—, where n is 0, 1, or 2,
—S(O)$_n$—O—, wherein n is 0, 1, or 2,
—P(O)($OR^{10}$)$_n$—, n is 0, 1, or 2, and
—S(O)$_2$—$NR^{10}$—, $R^t$ is selected from the group consisting of: $C_1$–$C_6$ alkyl, $C_3$–$C_6$ alkenyl, $C_3$–$C_{12}$ cycloalkyl, aryl, heteroaryl, and heterocycloalkyl, wherein said alkyl, alkenyl, cycloalkyl, aryl, heteroaryl, and heterocycloalkyl groups are optionally substituted by one or more substituents selected from Group A;

$R^w$ is H, $C_1$–$C_{10}$ alkyl, $C_3$–$C_{10}$ alkenyl, $C_3$–$C_{10}$ alkynyl, or $C_3$–$C_{10}$ cycloalkyl, wherein one or two carbons of said alkyl, cycloalkyl, alkenyl, alkynyl are optionally replaced by one or more heteroatoms selected from the group consisting of O, S and N, and are optionally substituted by one or more substituents selected from Group A;

$R^z$ is H, $C_1$–$C_{10}$ alkyl, $C_3$–$C_{10}$ alkenyl, $C_3$–$C_{10}$ alkynyl, or $C_3$–$C_{10}$ cycloalkyl, wherein one or two carbons of said alkyl, cycloalkyl, alkenyl, and alkynyl are optionally replaced by one or more heteroatoms selected from O, S and N, and are optionally substituted by one or more substituents selected from Group A.

4. The compound of claim 1 wherein $R^5$ is Me.

5. The compound of claim 1 wherein R is Et.

6. The compound of claim 1 wherein $R^2$ is H and $R^3$ is H.

7. The compound of claim 1 wherein T is —C(O)—NH— or wherein —C(O)—O—.

8. The compound of claim 1 wherein $R^1$ is $(CH_2)_m Z$.

9. The compound of claim 8 wherein m is 3.

10. The compound of claim 1 wherein Z is Z is quinolin-4-yl, 4-phenyl-1-imidazol-1-yl, imidazo(4,5-b)pyridin-3-yl, or 4-pyridin-3-yl-imidazol-1-yl.

11. The compound of claim 1 wherein $R^1=R^2=R^3=R^4$=H, and $R^5$ is —$CH_2$—CH=CH—Z.

12. The compound of claim 11 wherein Z is quinolin-2-yl, quinolin-3-yl, quinolin-4-yl, quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl.

13. The compound of claim 2 wherein $R^5$ is Me.

14. The compound of claim 2 wherein R is Et.

15. The compound of claim 2 wherein T is —C(O)—NH— or —C(O)—O—.

16. The compound of claim 2 wherein $R^1$ is $(CH_2)_m Z$.

17. The compound of claim 16 wherein m is 3.

18. The compound of claim 17 wherein Z is quinolin-4-yl, 4-phenyl-1-imidazol-1-yl, imidazo(4,5-b)pyridin-3-yl, or 4-pyridin-3-yl-imidazol-1-yl.

19. The compound of claim 2 wherein $R^1=R^w=R^x=R^4$=H, and $R^5$ is —$CH_2$—CH=CH—Z.

20. The compound of claim 19 wherein Z is quinolin-2-yl, quinolin-3-yl, quinolin-4-yl, quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl.

21. The compound of claim 3 wherein $R^5$ is Me.

22. The compound of claim 3 wherein $R^1$ is $(CH_2)_3 Z$.

23. The compound of claim 22 wherein Z is quinolin-4-yl, 4-phenyl-1-imidazol-1-yl, imidazo(4,5-b)pyridin-3-yl, or 4-pyridin-3-yl-imidazol-1-yl.

24. The compound of claim 3 wherein T is —C(O)—NH or —C(O)—O—.

25. The compound of claim 3 wherein R is Et.

26. The compound of claim 1 wherein said compound is selected from the group consisting of:

Compounds of formula 1, wherein R=Et, $R^1=R^2=R^3=R^4=R^6$=H, and $R^5$=($CH_2$)—CH=CH—Z, wherein Z is quinolin-2-yl, quinolin-3-yl, quinolin-4-yl, quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is absent, $R^t$ is H, acetyl, (4-methoxy)benzoyl, methanesulfonyl, Compounds of formula 1, wherein R=Et, $R^1=R^2=R^3=R^4=R^6$=H, and $R^5$=($CH_2$)—CH=CH—Z, wherein Z is quinolin-2-yl, quinolin-3-yl, quinolin-4-yl, quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is —S(O)$_2$, $R^t$ is —CH=$CH_2$, —$CH_2CH_2N(CH_3)_2$, —$CH_2CH_2$S-phenyl, Compounds of formula 1, wherein R=Et, $R^1=R^2=R^3=R^4=R^6$=H, $R^5$=($CH_2$)—CH=CH—Z, Z is quinolin-2-yl, quinolin-3-yl, quinolin-4-yl, quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is —C(O)—NH, $R^t$ is (2-nitrophenyl), phenyl, allyl, $CH(CH_3)_2$, cyclohexyl, Compounds of formula 1, wherein R=Et, $R^1$=Me, $R^2=R^3=R^4=R^6$=H, $R^5$=($CH_2$)—CH=CH—Z, Z is quinolin-2-yl, quinolin-3-yl, quinolin-4-yl, quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is absent, $R^t$ is H, acetyl, (4-methoxy)benzoyl, methanesulfonyl, Compounds of formula 1, wherein R=Et, $R^1$=Me, $R^2=R^3=R^4=R^6$=H, $R^5$=($CH_2$)—CH=CH—Z, Z is quinolin-2-yl, quinolin-3-yl, quinolin-4-yl, quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is —S(O)$_2$, $R^t$ is —CH=$CH_2$, —$CH_2CH_2N(CH_3)_2$, —$CH_2CH_2$S-phenyl, Compounds of formula 1, wherein R=Et, $R^1$=Me, $R^2=R^3=R^4=R^6$=H, $R^5$=($CH_2$)—CH=CH—Z, Z is quinolin-2-yl, quinolin-3-yl, quinolin-4-yl, quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is —C(O)—NH, $R^t$ is (2-nitrophenyl), phenyl, allyl, $CH(CH_3)_2$, cyclohexyl, Compounds of formula 1, wherein R=Et, $R^4$=Me, $R^1=R^2=R^3=R^6$=H, $R^5$=($CH_2$)—CH=CH—Z, Z is quinolin-2-yl, quinolin-3-yl, quinolin-4-yl, quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is absent, $R^t$ is H, acetyl, (4-methoxy)benzoyl, methanesulfonyl, Compounds of formula 1, wherein R=Et, $R^4$=Me, $R^1=R^2=R^3=R^6$=H, $R^5$=($CH_2$)—CH=CH—Z, Z is quinolin-2-yl, quinolin-3-yl, quinolin-4-yl, quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is —S(O)$_2$, R$^t$ is —CH=CH$_2$, —CH$_2$CH$_2$N(CH$_3$)$_2$, —CH$_2$CH$_2$S-phenyl, Compounds of formula 1, wherein R=Et, R$^4$=Me, R$^1$=R$^2$=R$^3$=R$^6$=H, R$^5$=(CH$_2$)—CH=CH—Z, Z is quinolin-2-yl, quinolin-3-yl, quinolin-4-yl , quinolin-5-yl, quinolin-6-yl, quinolin-7-yl, quinolin-8-yl , 4-phenyl-1-imidazol-1-yl, imidazo(4,5-b)pyridin-3-yl, or 4-pyridin-3yl-imidazol-1-yl, T is —C(O)—NH, R$^t$ is (2-nitrophenyl), phenyl, allyl, CH(CH$_3$)$_2$, cyclohexyl, Compounds of formula 1, wherein R=Et, R$^2$=R$^3$=Me, R$^1$=R$^4$=R$^6$=H, R$^5$=(CH$_2$)—CH=CH—Z, Z is quinolin-2-yl, quinolin-3-yl, quinolin-4-yl , quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is absent, R$^t$ is H, acetyl, (4-methoxy)benzoyl, methanesulfonyl, Compounds of formula 1, wherein R=Et, R$^2$=R$^3$=Me, R$^1$=R$^4$=R$^6$=H, R$^5$=(CH$_2$)—CH=CH—Z, Z is quinolin-2-yl, quinolin-3-yl, quinolin-4-yl , quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is —S(O)$_2$, R$^t$ is —CH=CH$_2$, —CH$_2$CH$_2$N(CH$_3$)$_2$, —CH$_2$CH$_2$S-phenyl, Compounds of formula 1, wherein R=Et, R$^2$=R$^3$=Me, R$^1$=R$^4$=R$^6$=H, R$^5$=(CH$_2$)—CH=CH—Z, Z is quinolin-2-yl, quinolin-3-yl, quinolin-4-yl , quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, TT is —C(O)—NH, R$^t$ is (2-nitrophenyl), phenyl, allyl, CH(CH$_3$)$_2$, cyclohexyl, Compounds of formula 1, wherein R=Et, R$^1$=R$^2$=R$^3$=R$^4$=R$^6$=H, R$^5$=Me, R$^1$=(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is absent, R$^t$ is acetyl, Compounds of formula 1, wherein R=Et, R$^2$=R$^3$=R$^4$=R$^6$=H, R$^5$=Me, R$^1$=(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is absent, R$^t$ is acetyl, Compounds of formula 1, wherein R=Et, R$^2$=R$^3$=R$^4$=R$^6$=H, R$^5$=Me, R$^1$=(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is absent, R$^t$ is (4-methoxy)benzoyl, Compounds of formula 1, wherein R=Et, R$^2$=R$^3$=R$^4$=R$^6$=H, R$^5$=Me, R$^1$=(CH$_2$)$_3$Z, Z is quinolin-4-yl, 4-phenyl-1-imidazol-1-yl, imidazo(4,5-b)pyridin-3-yl, or 4-pyridin-3yl-imidazol-1-yl, T is absent, R$^t$ is methanesulfonyl, Compounds of formula 1, wherein R=Et, R$^2$=R$^3$=R$^4$=R$^6$=H, R$^5$=Me, R$^1$=(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is —S(O)$_2$—, R$^t$ is —CH=CH$_2$, Compounds of formula 1, wherein R=Et, R$^2$=R$^3$=R$^4$=R$^6$=H, R$^5$=Me, R$^1$=(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is —S(O)$_2$—, R$^t$ is —CH$_2$CH$_2$N(CH$_3$)$_2$, Compounds of formula 1, wherein R=Et, R$^2$=R$^3$=R$^4$=R$^6$=H, R$^5$=Me, R$^1$=(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is —S(O)$_2$—, R$^t$ is CH$_2$CH$_2$—S-phenyl, Compounds of formula 1, wherein R=Et, R$^2$=R$^3$=R$^4$=R$^6$=H, R$^5$=Me, R$^1$=(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is —C(O)—NH—, R$^t$ is (2-nitrophenyl), Compounds of formula 1, wherein R=Et, R$^2$=R$^3$=R$^4$=R$^6$=H, R$^5$=Me, R$^1$=(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is —C(O)—NH—, R$^t$ is phenyl;

Compounds of formula 1, wherein R=Et, R$^2$=R$^3$=R$^4$=R$^6$=H, R$^5$=Me, R$^1$=(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is —C(O)NH—, R$^t$ is allyl, Compounds of formula 1, wherein R=Et, R$^2$=R$^3$=R$^4$=R$^6$=H, R$^5$=Me, R$^1$=(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is —C(O)—NH—, R$^t$ is CH(CH$_3$)$_2$, Compounds of formula 1, wherein R=Et, R$^2$=R$^3$=R$^4$=R$^6$=H, R$^5$=Me, R$^1$=(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is —C(O)—NH, R$^t$ is cyclohexyl, the pharmaceutically acceptable salts and prodrugs of the foregoing compounds.

27. The compound of claim 2 wherein said compound is selected from the group consisting of:

Compounds of formula 2, wherein R=Et, R$^1$=R$^w$=R$^x$=R$^4$=R$^6$=H, R$^5$=(CH$_2$)—CH=CH—Z, Z is quinolin-2-yl, quinolin-3-yl, quinolin-4-yl , quinolin-5-yl, quinolin-6-yl, quinolin-7-yl, quinolin-8-yl , 4-phenyl-1-imidazol-1-yl, imidazo(4,5-b)pyridin-3-yl, or 4-pyridin-3-yl-imidazol-1-yl, T is absent, R$^t$ is H, acetyl, (4-methoxy)benzoyl, methanesulfonyl, Compounds of formula 2, wherein R=Et, R$^1$=R$^w$=R$^x$=R$^4$=R$^6$=H, R$^5$=(CH$_2$)—CH=CH—Z, Z is quinolin-2-yl, quinolin-3-yl, quinolin-4-yl , quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is —S(O)$_2$, R$^t$ is —CH=CH$_2$, —CH$_2$CH$_2$N(CH$_3$)$_2$, —CH$_2$CH$_2$S-phenyl, Compounds of formula 2, wherein R=Et, R$^1$=R$^w$=R$^x$=R$^4$=R$^6$=H, R$^5$=(CH$_2$)—CH=CH—Z, Z is quinolin-2-yl, quinolin-3-yl, quinolin-4-yl , quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is —C(O)—NH, R$^t$ is (2-nitrophenyl), phenyl, allyl, CH(CH$_3$)$_2$, cyclohexyl, Compounds of formula 2, wherein R=Et, R$^w$=R$^x$=R$^4$=R$^6$=H, R$^5$=Me, R$^1$=(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is absent, R$^t$ is acetyl, Compounds of formula 2, wherein R=Et, R$^w$=R$^x$=R$^4$=R$^6$=H, R$^5$=Me, R$^1$=(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is absent, R$^t$ is acetyl, Compounds of formula 2, wherein R=Et, R$^w$=R$^x$=R$^4$=R$^6$=H, R$^5$=Me, R$^1$=(CH$_2$)$_3$Z, Z is quinolin-4-yl, 4-phenyl-1-imidazol-1-yl, imidazo(4,5-b)pyridin-3-yl, or 4-pyridin-3-yl-imidazol-1-yl, T is absent, R$^t$ is (4-methoxy)benzoyl, Compounds of formula 2, wherein $R^w=R^x=R^4=R^6=H$, $R^5=Me$, $R^1=(CH_2)_3Z$, Z is quinolin-4-yl, 4-phenyl-1-imidazol-1-yl, imidazo(4,5-b)pyridin-3-yl, or 4-pyridin-3-yl-imidazol-1-yl, T is absent, $R^t$ is methanesulfonyl, Compounds of formula 2, wherein $R^w=R^x=R^4=R^6=H$, $R^5=Me$, $R^1=(CH_2)_3Z$, Z is quinolin-4-yl, 4-phenyl-1-imidazol-1-yl, imidazo(4,5-b)pyridin-3-yl, or 4-pyridin-3-yl-imidazol-1-yl, T is $-S(O)_2-$, $R^t$ is $-CH=CH_2$, Compounds of formula 2, wherein R=Et, $R^w=R^x=R^4=R^6=H$, $R^5=Me$, $R^1=(CH_2)_3Z$, Z is quinolin-4-yl, 4-phenyl-1-imidazol-1-yl, imidazo(4,5-b)pyridin-3-yl, or 4-pyridin-3-yl-imidazol-1-yl, T is $-S(O)_2-$, $R^t$ is $-CH_2CH_2N(CH_3)_2$, Compounds of formula 2, wherein R=Et, $R^w=R^x=R^4=R^6=H$, $R^5=Me$, $R^1=(CH_2)_3Z$, Z is quinolin-4-yl, 4-phenyl-1-imidazol-1-yl, imidazo(4,5-b)pyridin-3-yl, or 4-pyridin-3-yl-imidazol-1-yl, T is $-S(O)_2-$, $R^t$ is $CH_2CH_2-S$-phenyl, Compounds of formula 2, wherein R=Et, $R^w=R^x=R^4=R^6=H$, $R^5=Me$, $R^1=(CH_2)_3Z$, Z is quinolin-4-yl, 4-phenyl-1-imidazol-1-yl, imidazo(4,5-b)pyridin-3-yl, or 4-pyridin-3-yl-imidazol-1-yl, T is $-C(O)-NH-$, $R^t$ is (2-nitrophenyl), Compounds of formula 2, wherein R=Et, $R^w=R^x=R^4=R^6=H$, $R^5=Me$, $R^1=(CH_2)_3Z$, Z is quinolin-4-yl, 4-phenyl-1-imidazol-1-yl, imidazo(4,5-b)pyridin-3-yl, or 4-pyridin-3-yl-imidazol-1-yl, T is $-C(O)-NH-$, $R^t$ is phenyl, Compounds of formula 2, wherein R=Et, $R^w=R^x=R^4=R^6=H$, $R^5=Me$, $R^1=(CH_2)_3Z$, Z is quinolin-4-yl, 4-phenyl-1-imidazol-1-yl, imidazo(4,5-b)pyridin-3-yl, or 4-pyridin-3-yl-imidazol-1-yl, T is $-C(O)NH-$, $R^t$ is allyl, Compounds of formula 2, wherein R=Et, $R^w=R^x=R^4=R^6=H$, $R^5=Me$, $R^1=(CH_2)_3Z$, Z is quinolin-4-yl, 4-phenyl-1-imidazol-1-yl, imidazo(4,5-b)pyridin-3-yl, or 4-pyridin-3-yl-imidazol-1-yl, T is $-C(O)-NH-$, $R^t$ is $CH(CH_3)_2$, Compounds of formula 2, wherein R=Et, $R^w=R^x=R^4=R^6=H$, $R^5=Me$, $R^1=(CH_2)_3Z$, Z is quinolin-4-yl, 4-phenyl-1-imidazol-1-yl, imidazo(4,5-b)pyridin-3-yl, or 4-pyridin-3-yl-imidazol-1-yl, T is $-C(O)-NH$, $R^t$ is cyclohexyl, the pharmaceutically acceptable salts and prodrugs of the foregoing compounds.

28. The compound of claim 3, wherein said compound is selected from the group consisting of:

Compounds of formula 3, wherein R=Et, $R^1=R^w=R^6=H$, $R^z=Me$, $R^5=(-CH_2)-CH=CH-Z$, Z is quinolin-2-yl, quinolin-3-yl, quinolin-4-yl, quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is absent, $R^t$ is H, acetyl, (4-methoxy)benzoyl, methanesulfonyl, Compounds of formula 3, wherein R=Et, $R^1=R^w=R^6=H$, $R^z=Me$, $R^5=-(CH_2)-CH=CH-Z$, Z is quinolin-2-yl, quinolin-3-yl, quinolin-4-yl, quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is $-S(O)_2$, $R^t$ is $-CH=CH_2$, $-CH_2CH_2N(CH_3)_2$, $-CH_2CH_2S$-phenyl, Compounds of formula 3, wherein R=Et, $R^1=R^w=R^6=H$, $R^z=Me$, $R^5=-(CH_2)-CH=CH-Z$, Z is quinolin-2-yl, quinolin-3-yl, quinolin-4-yl, quinolin-5-yl, quinolin-6-yl, quinolin-7-yl, quinolin-8-yl, 4-phenyl-1-imidazol-1-yl, imidazo(4,5-b)pyridin-3-yl, or 4-pyridin-3-yl-imidazol-1-yl, T is $-C(O)-NH$, $R^t$ is (2-nitrophenyl), phenyl, allyl, $-CH(CH_3)_2$, cyclohexyl, Compounds of formula 3, wherein R=Et, $R^w=R^6=H$, $R^5=R^z=Me$, $R^1=-(CH_2)_3Z$, Z is quinolin-4-yl, 4-phenyl-1-imidazol-1-yl, imidazo(4,5-b)pyridin-3-yl, or 4-pyridin-3-yl-imidazol-1-yl, T is absent, $R^t$ is acetyl, Compounds of formula 3, wherein R=Et, $R^w=R^6=H$, $R^5=R^z=Me$, $R^1=-(CH_2)_3Z$, Z is quinolin-4-yl, 4-phenyl-1-imidazol-1-yl, imidazo(4,5-b)pyridin-3-yl, or 4-pyridin-3-yl-imidazol-1-yl, T is absent, $R^t$ is (4-methoxy)benzoyl, Compounds of formula 3, wherein R=Et, $R^w=R^6=H$, $R^5=R^z=Me$, $R^1=-(CH_2)_3Z$, Z is quinolin-4-yl, 4-phenyl-1-imidazol-1-yl, imidazo(4,5-b)pyridin-3-yl, or 4-pyridin-3-yl-imidazol-1-yl, T is absent, $R^t$ is methanesulfonyl, Compounds of formula 3, wherein R=Et, $R^w=R^6=H$, $R^5=R^z=Me$, $R^1=-(CH_2)_3Z$, Z is quinolin-4-yl, 4-phenyl-1-imidazol-1-yl, imidazo(4,5-b)pyridin-3-yl, or 4-pyridin-3-yl-imidazol-1-yl, T is $-S(O)_2-$, $R^t$ is $-CH=CH_2$, Compounds of formula 3, wherein R=Et, $R^w=R^6=H$, $R^5=R^z=Me$, $R^1=-(CH_2)_3Z$, Z is quinolin-4-yl, 4-phenyl-1-imidazol-1-yl, imidazo(4,5-b)pyridin-3-yl, or 4-pyridin-3-yl-imidazol-1-yl, T is $-S(O)_2-$, $R^t$ is $-CH_2CH_2N(CH_3)_2$, Compounds of formula 3, wherein R=Et, $R^w=R^6=H$, $R^5=R^z=Me$, $R^1=-(CH_2)_3Z$, Z is quinolin-4-yl, 4-phenyl-1-imidazol-1-yl, imidazo(4,5-b)pyridin-3-yl, or 4-pyridin-3-yl-imidazol-1-yl, T is $-S(O)_2-$, $R^t$ is $-CH_2CH_2-S$-phenyl, Compounds of formula 3, wherein R=Et, $R^w=R^6=H$, $R^5=R^z=Me$, $R^1=-(CH_2)_3Z$, Z is quinolin-4-yl, 4-phenyl-1-imidazol-1-yl, imidazo(4,5-b)pyridin-3-yl, or 4-pyridin-3-yl-imidazol-1-yl, T is $-C(O)-NH-$, $R^t$ is (2-nitrophenyl), Compounds of formula 3, wherein R=Et, $R^w=R^6=H$, $R^5=R^z=Me$, $R^1=-(CH_2)_3Z$, Z is quinolin-4-yl, 4-phenyl-1-imidazol-1-yl, imidazo(4,5-b)pyridin-3-yl, or 4-pyridin-3-yl-imidazol-1-yl, T is $-C(O)-NH-$, $R^t$ is phenyl, Compounds of formula 3, wherein R=Et, $R^w=R^6=H$, $R^5=R^z=Me$, $R^1=-(CH_2)_3Z$, Z is quinolin-4-yl, 4-phenyl-1-imidazol-1-yl, imidazo(4,5-b)pyridin-3-yl, or 4-pyridin-3-yl-imidazol-1-yl, T is $-C(O)-NH-$, $R^t$ is allyl, Compounds of formula 3, wherein R=Et, $R^w=R^6=H$, $R^5=R^z=Me$, $R^1=-(CH_2)_3Z$, Z is quinolin-4-yl, 4-phenyl-1-imidazol-1-yl, imidazo(4,5-b)pyridin-3-yl, or 4-pyridin-3-yl-imidazol-1-yl, T is $-C(O)-NH-$, $R^t$ is $-CH(CH_3)_2$;

Compounds of formula 3, wherein R=Et, $R^w=R^6=H$, $R^5=R^z=Me$, $R^1=-(CH_2)_3Z$, Z is quinolin-4-yl, 4-phenyl-1-imidazol-1-yl, imidazo(4,5-b)pyridin-3-yl, or 4-pyridin-3-yl-imidazol-1-yl, T is $-C(O)-NH-$, $R^t$ is cyclohexyl;

the pharmaceutically acceptable salts and prodrugs of the foregoing compounds.

29. A method of preparing a compound of the formula I in claim 1:

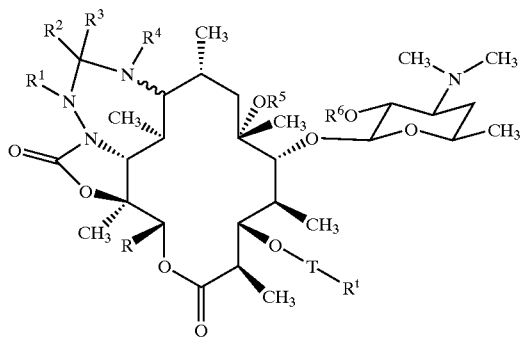

or pharmaceutically acceptable salts thereof, which comprises the steps of treating a compound of the formula 7

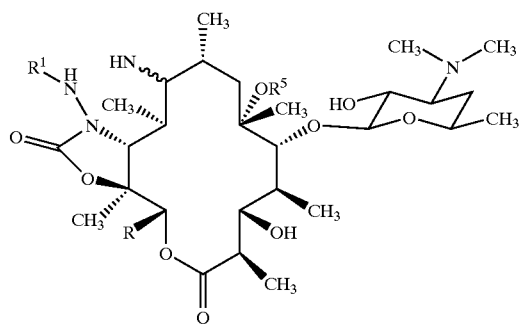

with a compound of formula $R^2R^3C(=O)$ in the presence of an acid in a solvent and then effecting either alkylation or reductive alkylation.

30. The method of claim 29 wherein the acid is selected from the group consisting of formic acid, acetic acid, p-toluenesulfonic acid and the solvents are selected from THF, dichloromethane, chloroform.

31. A pharmaceutical composition for the treatment of a bacterial or protozoa infection in a mammal, fish or bird which comprises a therapeutically effective amount of a compound of claim 1, and a pharmaceutically acceptable carrier.

32. A pharmaceutical composition for the treatment of a bacterial or protozoa infection in a mammal, fish or bird which comprises a therapeutically effective amount of a compound of claim 2, and a pharmaceutically acceptable carrier.

33. A pharmaceutical composition for the treatment of a bacterial or protozoa infection in a mammal, fish or bird which comprises a therapeutically effective amount of a compound of claim 3, and a pharmaceutically acceptable carrier.

34. A method of treating a bacterial or protozoa infection in a mammal, fish, or bird, which comprises administering to said mammal, fish, or bird a therapeutically effective amount of a compound of claim 1.

35. A method of treating a bacterial or protozoa infection in a mammal, fish, or bird, which comprises administering to said mammal, fish, or bird a therapeutically effective amount of a compound of claim 2.

36. A method of treating a bacterial or protozoa infection in a mammal, fish, or bird, which comprises administering to said mammal, fish, or bird a therapeutically effective amount of a compound of claim 3.

* * * * *